United States Patent
Zhang et al.

(10) Patent No.: US 11,214,554 B2
(45) Date of Patent: Jan. 4, 2022

(54) INDOLEAMINE 2,3-DIOXYGENASE INHIBITOR, METHOD FOR PREPARATION AND USE THEREOF

(71) Applicant: NANJING HUAWE MEDICINE TECHNOLOGY GROUP CO., LTD., Jiangsu (CN)

(72) Inventors: Xiaoqing Zhang, Jiangsu (CN); Zhichun Song, Jiangsu (CN); Jinyuan Bao, Jiangsu (CN)

(73) Assignee: NANJING HUAWE MEDICINE TECHNOLOGY GROUP CO., LTD., Jiangsu (CN)

( * ) Notice: Subject to any disclaimer, the term of this patent is extended or adjusted under 35 U.S.C. 154(b) by 0 days.

(21) Appl. No.: 15/733,410

(22) PCT Filed: Dec. 13, 2018

(86) PCT No.: PCT/CN2018/120771
§ 371 (c)(1),
(2) Date: Jul. 22, 2020

(87) PCT Pub. No.: WO2019/141027
PCT Pub. Date: Jul. 25, 2019

(65) Prior Publication Data
US 2021/0094924 A1    Apr. 1, 2021

(30) Foreign Application Priority Data
Jan. 22, 2018  (CN) .................. 201810058615.8

(51) Int. Cl.
| | | |
|---|---|---|
| *C07D 271/08* | (2006.01) |
| *C07D 413/04* | (2006.01) |
| *C07D 413/08* | (2006.01) |
| *C07D 417/12* | (2006.01) |

(52) U.S. Cl.
CPC ......... *C07D 271/08* (2013.01); *C07D 413/04* (2013.01); *C07D 413/08* (2013.01); *C07D 417/12* (2013.01)

(58) Field of Classification Search
CPC ... C07D 271/08; C07D 413/04; C07D 417/12
See application file for complete search history.

(56) References Cited

FOREIGN PATENT DOCUMENTS

| | | |
|---|---|---|
| CN | 102164902 A | 8/2011 |
| CN | 103130735 A | 6/2013 |
| CN | 106883193 A | 6/2017 |
| CN | 107304191 A | 10/2017 |
| CN | 107954999 A | 4/2018 |
| CN | 108689958 A | 10/2018 |
| CN | 108863976 A | 11/2018 |
| WO | 2006122150 A1 | 11/2006 |
| WO | 2010005958 A2 | 1/2010 |
| WO | 2014066834 A1 | 5/2014 |
| WO | 2016071293 A2 | 5/2016 |
| WO | 2016155545 A1 | 10/2016 |

*Primary Examiner* — Kamal A Saeed
(74) *Attorney, Agent, or Firm* — Novick, Kim & Lee, PLLC; Allen Xue

(57) ABSTRACT

A novel indoleamine 2,3-dioxygenase inhibitor and/or its pharmaceutically acceptable salts can used, in the preparation of a drug for indoleamine 2,3-dioxygenase (IDO) related diseases, such as cancer, Alzheimer's, depression, cataract, etc.

11 Claims, No Drawings

INDOLEAMINE 2,3-DIOXYGENASE INHIBITOR, METHOD FOR PREPARATION AND USE THEREOF

TECHNICAL FIELD

The technical field of the present application relates to the medicinal chemistry, and specifically relates to an efficient IDO inhibitor, method for preparation and use thereof.

BACKGROUND

Indoleamine 2,3-dioxygenase (IDO) is the only extrahepatic rate limiting enzyme that catalyzes the catabolism of tryptophan along the kynurenine pathway, and is widely distributed in many tissues and cells of human and animals. IDO can inhibit the proliferation of pathogenic microorganisms by reducing the concentration of tryptophan in the microenvironment. IDO is also closely related to nervous system diseases, and can reduce the level of 5-hydroxytryptamine and cause depression and can also cause the accumulation of neurotoxic metabolites such as quinoline acids in the brain. Some evidences show that IDO participates in the induction of immune tolerance.

Studies on pregnancy, tumor resistance, chronic infections and autoimmune diseases in mammals have shown that cells expressing IDO can inhibit T-cell responses and promote tolerance. Therefore, IDO plays an important role in the regulation of metabolic immunity in the inhibition of T-cell immunity and anti-tumor immunity, induction of maternal-fetal immune tolerance and transplant immune tolerance. At present, IDO is an important drug discovery target and has become the most important small molecular regulatory target of anti-tumor immunotherapy.

At present, there is no IDO inhibitor drug on the domestic and foreign market. The compounds that had entered clinical trials abroad are the compound NLG919 and Indoximod (NLG-8189) from the New Link Genetics Corporation, the United States; and the compound INCB024360 (Epacadostat) from the Incyte Corporation, the United States, respectively; wherein, the use of Epacadostat and an immune checkpoint inhibitor (Yervoy) in combination had shown good efficacy. Currently Epacadostat is in phase III clinical research and Epacadostat analogs are also in the phase II clinical phase, with studies suggesting both Epacadostat and its analogs will be marketed as IDO inhibitor drugs with high potential.

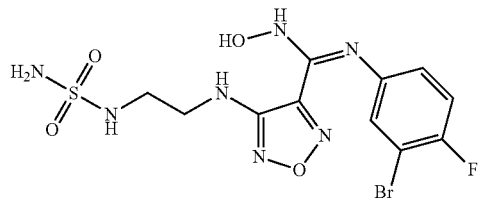

structure of INCB024360

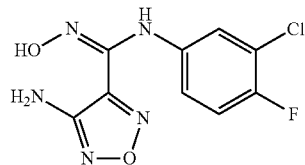

structure of INCB024360 analog

Invention patent applications involving IDO inhibitors include WO2006122150, WO2016071293, WO2010005958, WO2014066834, WO2016155545, CN 103130735 A, CN102164902 etc.

The invention patent application CN102164902 discloses the following compounds with good clinical research results:

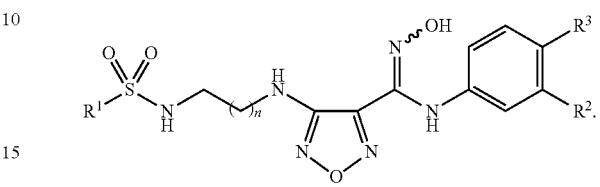

CN106883193A discloses the following compounds:

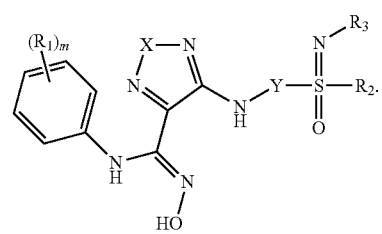

CN105646389 A discloses the following compounds:

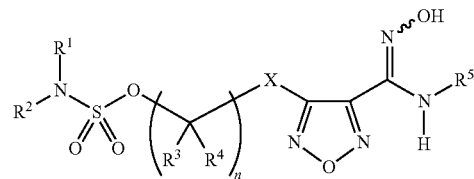

wherein, the definition of respective substituent is as described in the specification.

At present, there are still high technical barriers to the research and development of IDO inhibitors. None of the existing me-too IDO inhibitor molecules had been used in clinical treatments. IDO inhibitors, as drugs with new targets and new mechanisms, may be used to treat tumors, Alzheimer's disease, depression, cataract and other major diseases, and thus have a very good market value. In order to meet the clinical needs to IDO regulation metabolites and achieve better disease treatment effects, we are committed to the research and development of a series of high-efficiency and low-toxicity IDO inhibitors, which is of great significance in the field of medicine.

SUMMARY

The object of the invention is to provide a novel indoleamine 2,3-dioxygenase inhibitor and a method for preparation thereof.

Another object of the invention is to provide a pharmaceutical composition of the indoleamine 2,3-dioxygenase inhibitor and the use thereof.

The object of the invention can be achieved by the following measures.

A compound and a salt or isomer thereof, characterized in that the structure of the compound is shown in formula I or formula II:

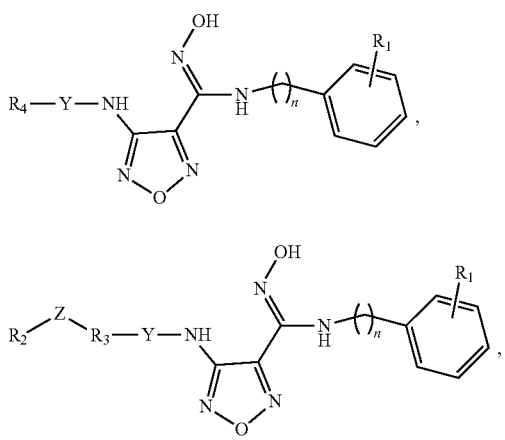

wherein, the group $R_1$ is arbitrarily selected from one or more of hydrogen atom, halogen and trifluoromethyl;

n represents 0 or 1;

Y is arbitrarily selected from one of oxygen atom, sulfur atom, nitrogen atom or

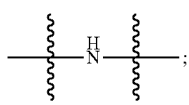

Z is arbitrarily selected from one of oxygen atom, sulfur atom, nitrogen atom and

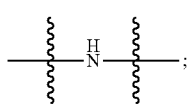 [SMILES: *N*]

The group $R_3$ is arbitrarily selected from a substituted or unsubstituted $C_{1\sim10}$ alkyl, $C_{3\sim10}$ cycloalkyl, and the substituent is arbitrarily selected from one or more of amino, oxy, $C_{3\sim6}$ cycloalkyl, $C_{2\sim6}$ ester group, $C_{1\sim6}$ alkyl hydroxyl group, —$CONH_2$;

$R_4$ is arbitrarily selected from one of hydrogen atom,

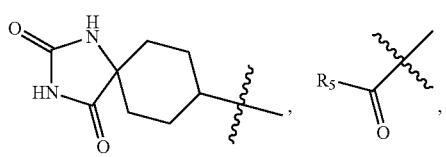

and a substituted or unsubstituted $C_{1\sim10}$ alkyl; Further, the substituent of the $C_{1\sim10}$ alkyl is arbitrarily selected from one or more of

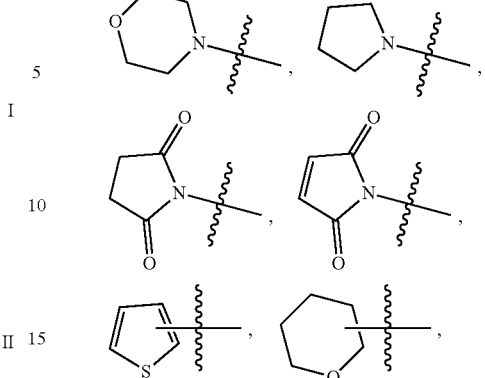

unsubstituted phenyl or phenyl substituted with $C_{1\sim4}$ alkyl;

The group $R_2$ is arbitrarily selected from one of hydrogen atom, $C_{1\sim6}$ alkyl, $C_{2\sim6}$ ester group,

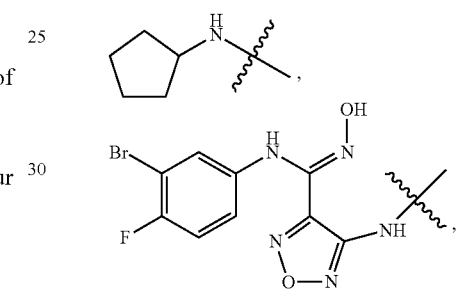

sulfonyl substituted with $C_{1\sim4}$ alkyl, sulfonyl substituted with amino, sulfonamido substituted with amino,

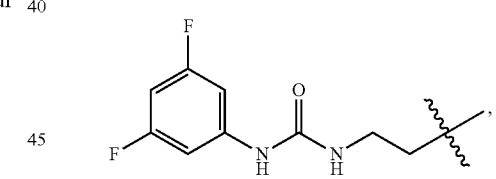

substituted or unsubstituted $C_{4\sim8}$ aryl or heteroaryl

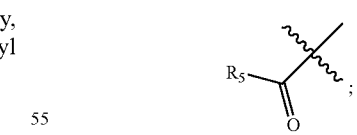

$R_5$ is arbitrarily selected from one of $C_{1\sim6}$ alkyl, $C_{1\sim6}$ alkoxy, substituted or unsubstituted anilino, substituted or unsubstituted $C_{5\sim12}$ aryl or $C_{4\sim10}$ heteroaryl, and the substituents on the anilino, aryl and heteroaryl are any one or more of halogen and amino.

In one embodiment, Z and $R_3$ are taken together to form a 5-8 membered heterocycloalkyl;

In one embodiment, Y, Z and $R_3$ are taken together to form a 5-8 membered heterocycloalkyl;

In one embodiment, $R_2$ is

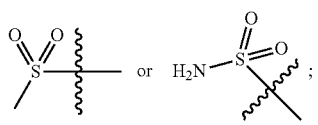;

In one embodiment, n represents 1, $R_2$

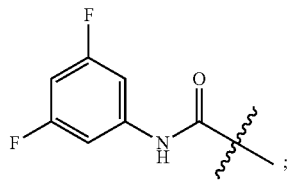 [SMILES: *C(=O)Nc1cc(F)cc(F)c1];

In one embodiment, the group $R_4$ is selected from a $C_{1-10}$ alkyl, which is terminated with one of

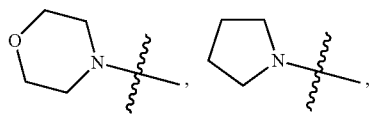,

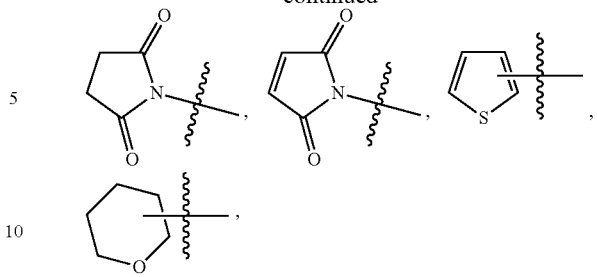

a unsubstituted phenyl or a phenyl substituted with $C_{1-4}$ alkyl.

The invention also provides methods for preparing compounds of formula I and formula II and their salts or isomers, but is not limited to the methods described below. All raw materials are prepared according to characteristics of groups in the target molecules in accordance with the general formula, by the methods in these schemes and methods well known to those of ordinary skill in the organic chemistry field, or purchased directly. The compounds of the invention may be synthesized by combining the following methods with synthetic methods known in the field of synthetic organic chemistry or related modifications recognized by those skilled in the art.

The Preparation Scheme of Formula I:

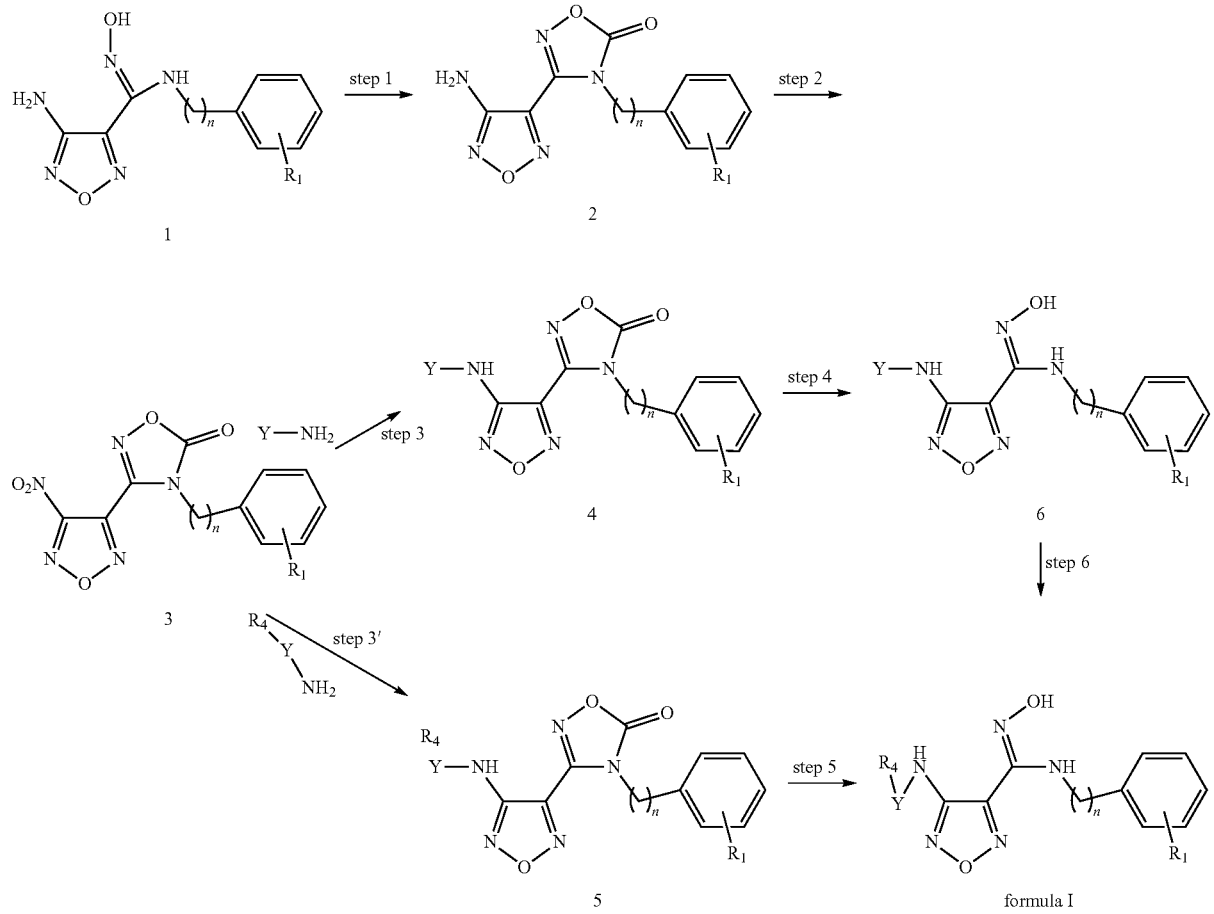

Preparation Scheme of Formula I

In the above preparation scheme of formula I, the definitions of n, and the groups $R_1$, $R_4$ and Y are the same as those defined above in the specification, wherein, the preparation of compound 1 can be performed by referring to the method disclosed in the specification of invention patent WO2010005958.

The method for preparation of the compound of formula I and the salts or isomers thereof comprises the following steps:

step 1: a ring closure reaction is carried out under the action of N,N'-carbonyldiimidazole to obtain the compound of general formula 2, using the compound of general formula 1 as the starting material;

step 2: the compound 2 is subjected to a conventional oxidation reaction under the action of an oxidant to obtain the compound of general formula 3. The oxidants include but are not limited to: hydrogen peroxide, potassium permanganate and manganese dioxide. The temperature of the oxidation reaction is from room temperature to 100° C.

step 3: in one embodiment, when $R_4$ is group

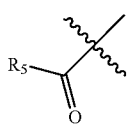

(the definitions of the group $R_5$ are the same as those defined above in the specification), the compound of general formula 3 is dissolved in an organic solvent, and slowly added with an aqueous solution of Y—$NH_2$ compound such as 10%-20% hydrazine hydrate, methylhydrazine, hydroxylamine, or thiamine, to obtain the compound of general formula 4.

step 4: the compound of general formula 4 is subjected to a ring-opening reaction under the action of a base to obtain the compound of general formula 6;

step 6: the compound of general formula 6 is reacted with an acid chloride or isocyanate compound containing the group $R_5$ to obtain the compound of general formula I, and the temperature of the reaction is 15° C. to 50° C. In another embodiment, when $R_4$ is arbitrarily selected from H,

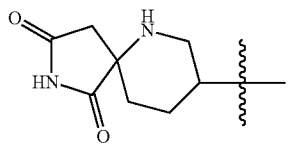

and a substituted or unsubstituted $C_{1~10}$ alkyl, the preparation of the compound of formula I further includes the following steps:

step3':
the compound of general formula 3 is dissolved in an organic solvent, and then added with the organic solution of the $R_4$—Y—$NH_2$ compound dropwise to react to obtain the compound of general formula 5.

step 5:
the compound of general formula 5 is dissolved in an organic solvent, and then is subjected to a ring-opening reaction under the action of a base to obtain the compound of formula I.

The Preparation Scheme of Formula II:

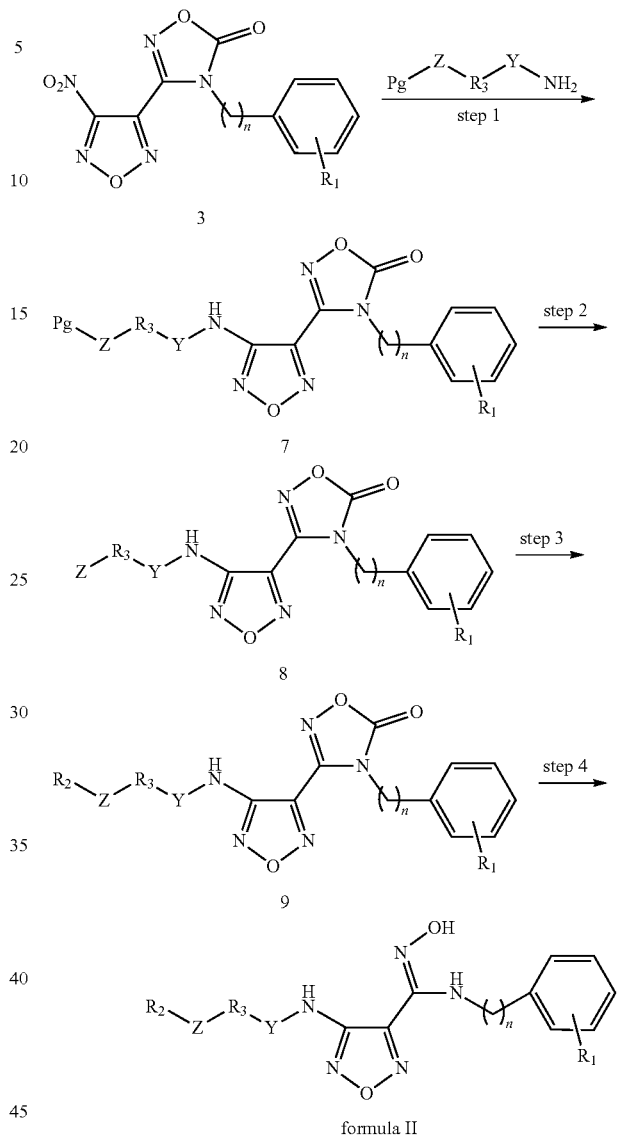

Preparation Scheme of Formula II

In the above preparation scheme of formula IL, the definitions of n, and the groups $R_1$, $R_3$, Z and Y are the same with those defined above in the specification. The method for preparation of the compound of formula II and the salts or isomers thereof includes the following steps:

step1: the appropriate compound of general formula 3 is selected, dissolved in an organic solvent and added dropwise with an organic solution of

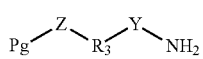

to obtain the compound of general formula 7; wherein, Pg is a protective group for hydroxyl, mercapto or amino, such as Boc, Cbz, Fmoc, methyl or acetyl, etc.

step 2: the compound of general formula 7 is deprotected under the action of hydrochloric acid, trifluoroacetic acid, piperidine, palladium on carbon/hydrogen or sodium hydroxide, etc., to obtain the compound of the general formula 8;

step3: any one of $R_2$-containing carboxylic acid compounds, $R_2$-containing acid chlorides or sulfonyl chloride compounds, $R_2$-containing halides or $R_2$-containing isocyanates is selected according to the structural characteristics of the target molecule to react with the compound of general formula 8 under basic condition to obtain the compound of general formula 9;

step 4: the compound of general formula 9 is subjected to a ring-opening reaction under the action of a base to obtain the compound of formula II.

In the above methods for preparation, when the group protection is performed to meet the demand of the stability of each intermediate in the preparation process, the corresponding intermediates need to be deprotected beforehand to finally obtain the target molecular compounds. If the methods for preparing the compound involve protecting and deprotecting various chemical groups, those skilled in the art can easily determine the needs for protection and deprotection and select suitable protecting groups. The deprotection reaction can be carried out under the catalytic action of trifluoroacetic acid or hydrochloric acid.

The above-mentioned features mentioned in the present disclosure, or the features mentioned in the working examples can be arbitrarily combined conforming to the laws of pharmacy, and each feature disclosed in the specification can be replaced by any alternative feature providing the same, equal or similar purpose. Unless otherwise specified, the disclosed features are only general examples with the same or similar features.

Another aspect of the invention provides a pharmaceutical composition containing a therapeutically effective amount of the compound of formula I or formula II or the pharmaceutically acceptable salts or isomers thereof as an active ingredient, and one or more pharmaceutically acceptable carriers, diluents or excipients.

The pharmaceutical composition preferably contains the pharmaceutically acceptable salts or isomers of formula I or formula II as an active ingredient in a weight ratio of 1% to 90%, and more preferably contains the active ingredient in a weight ratio of 10% to 80%.

Unless otherwise specified, the following terms used in the claims and the specification have the following meanings or characteristics:

The term "aryl" means an all-carbon monocyclic or fused polycyclic group having 5 to 12 carbon atoms, with a completely conjugated a electron system. Non-limiting examples of aryl groups include, but are not limited to phenyl, naphthyl and anthracenyl. The aryl ring may be fused to a heteroaryl, heterocyclic or cycloalkyl ring, wherein the ring connected to the parent structure is an aryl ring. The aryl group may be substituted or unsubstituted. When substituted, the substituents are preferably one or more, more preferably one, two or three, and still more preferably one or two, groups independently selected from the group consisting of lower alkyl, trihaloalkyl, halogen, hydroxyl, lower alkoxy, mercapto, (lower alkyl)thio, cyano, acyl, thioacyl, O-carbamoyl, N-carbamoyl, O-thiocarbamoyl, N-thiocarbamoyl, C-amido, N-amido, nitro, N-sulfonamido, S-sulfonamido. Preferably, the aryl group is a 5-membered monocyclic aryl group or a 6-membered monocyclic aryl group.

The term "heteroaryl" means a monocyclic or fused ring group having 5 to 12 ring atoms, containing one, two, three or four ring heteroatoms selected from N, O or S, with the remaining ring atoms being selected form C, and with a completely conjugated a electron system. The heteroaryl ring may be fused to an aryl group, heterocyclic group or cycloalkyl ring, wherein the ring connected to the parent structure is a heteroaryl ring. The heteroaryl groups may be substituted or unsubstituted. When substituted, the substituent is preferably one or more, more preferably one, two or three, and still more preferably one or two groups. Non-limiting examples of unsubstituted heteroaryl include, but are not limited to pyrrole, furan, thiophene, imidazole, oxazole, thiazole, pyrazole, pyrimidine, quinoline, isoquinoline, purine, tetrazole, triazine, and carbazole; preferably, the heteroaryl group is a nitrogen-containing 5-membered monocyclic heteroaryl group or a nitrogen-containing 6-membered monocyclic heteroaryl group.

The term "alkyl" means a saturated aliphatic hydrocarbon group having 1-20 carbon atoms, including straight-chain and branched-chain groups (the numerical range mentioned in this application, for example "1-20", means that this group, which is an alkyl group, may contain 1 carbon atom, 2 carbon atoms, 3 carbon atoms, etc., and up to 20 carbon atoms). The alkyl group in the invention includes "alkylene group". An alkyl group containing 1 to 6 carbon atoms is referred as a lower alkyl group. When the lower alkyl group has no substituent, it is referred as an unsubstituted lower alkyl group. More preferably, the alkyl group is a medium-sized alkyl group having 1 to 10 carbon atoms, such as methyl, ethyl, ethylene, propyl, propylene, 2-propyl, n-butyl, isobutyl, butylene, tert-butyl, pentyl, etc. Most preferably, the alkyl group is a lower alkyl group having 1 to 5 carbon atoms, such as methyl, ethyl, propyl, 2-propyl, n-butyl, butylene, isobutyl or tert-butyl etc. The alkyl group may be substituted or unsubstituted.

The term "alkoxy" means —O-(unsubstituted alkyl) and —O-(unsubstituted cycloalkyl), where the definition of alkyl is the same as defined above in the specification. "Alkoxy" preferably includes alkoxy of 1 to 10 carbon atoms, more preferably alkoxy of 1 to 6 carbon atoms; representative examples thereof include, but are not limited to, methoxy, ethoxy, propoxy, butoxy, cyclopropoxy, cyclobutoxy, cyclopentyloxy, cyclohexyloxy, etc.

The term "trifluoromethyl" means —$CF_3$.

The term "isomer" is selected from a cis isomer, trans isomer or a mixture of cis and trans isomers.

The term "halogen" means fluorine, chlorine, bromine or iodine.

The term "amino" means —$NH_2$.

When a carbonyl group is used as a substituent, it is referred as an oxo group.

The term "alkylhydroxyl" means —R—OH, where R is as defined for alkyl.

The term "sulfonyl" means

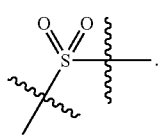 [SMILES: *S(*)(=O)=O]

The term "sulfonamido" means

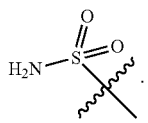

The term "mercapto" means —SH.

The term "cycloalkyl" means a saturated or partially unsaturated monocyclic or polycyclic cyclic hydrocarbon substituent, which includes 3 to 20 carbon atoms, preferably 3 to 12 carbon atoms, more preferably the cycloalkyl ring containing 3 to 8 carbon atoms, most preferably the cycloalkyl ring containing 3 to 6 carbon atoms, most preferably cyclopropyl. Non-limiting examples of monocyclic cycloalkyls include cyclopropyl, cyclobutyl, cyclopentyl, cyclopentenyl, cyclohexyl, cyclohexenyl, cyclohexadienyl, cycloheptyl, cycloheptatrienyl, cyclooctyl and the like, and preferably cyclopropyl and cyclohexenyl.

The term "heterocycloalkyl" refers to a saturated monocyclic or polycyclic cyclic hydrocarbon substituent in which one or more ring atoms are selected from heteroatoms of nitrogen, oxygen, or sulfur, and the remaining ring atoms of the substituent are carbon.

The term "ester" refers to the ester functionality in the carboxylic acid derivative, —COOR (R is generally a non-H group such as alkyl, and the definition of alkyl is as described above). For example, when the number of carbon atoms in the alkyl group is 1 to 6, the ester group may be abbreviated as $C_{1\sim 6}$ ester group.

The term "pharmaceutically acceptable salts" refers to those salts that retain the biological effectiveness and properties of the parent compound. Such salts include but are not limited to salts formed with acids, which are obtained by the reaction of the free base of the parent compound with inorganic acids or organic acids. An inorganic acid is such as (but not limited to) hydrochloric acid, hydrobromic acid, etc. and an organic acid is such as (but not limited to) acetic acid, malic acid, fumaric acid, maleic acid, p-toluenesulfonic acid, tartaric acid, citric acid, lactic acid, succinic acid or malonic acid etc. Such salts are used in mammals for safety, effectiveness, and proper biological activity.

"Pharmaceutical composition" refers to a mixture of one or more compounds or their pharmaceutically acceptable salts, isomers, prodrugs, etc. described herein, and other chemical components, such as pharmaceutically acceptable carriers and excipients. The purpose of providing the pharmaceutical composition is to facilitate the administration of the compound to an organism.

"Pharmaceutically acceptable carrier" refers to a carrier or diluent that does not cause significant irritation to the organism and does not interfere with the biological activity and properties of the administered compounds.

"Excipient" refers to an inert substance added to a pharmaceutical composition to further facilitate administration of the compounds. Examples of excipients include (but are not limited to) lactose, glucose, sucrose, microcrystalline cellulose, sorbitol, polyvinylpyrrolidone, cellulose, water, methyl cellulose, and the like.

The pharmaceutical composition may also contain: lubricants such as talc, magnesium stearate and mineral oil; wetting agents; emulsifiers and suspending agents; preservatives such as methyl benzoate and hydroxypropyl benzoate; sweeteners and flavors. The compositions of the invention may be formulated by using methods known in the art in order to provide the effect of immediate release, sustained release, or delayed release of the active ingredients after administration to a patient.

The invention also provides the use of the compound of formula I or formula II and the pharmaceutically acceptable salt or isomer thereof for:

(1) preparation of drugs for diseases related to indoleamine 2,3-dioxygenase (IDO);

(2) preparation of drugs for diseases related to disorders of tryptophan metabolism.

Further, the compound of the present disclosure can be used to prepare medicines for tumors, Alzheimer's disease, depression, cataract and other major diseases.

Preliminary drug activity research results indicate that the compounds of the invention have good IDO inhibitory activity, and can be used to prepare drugs for preventing and/or treating diseases with pathological features of tryptophan metabolism pathway mediated by IDO. The pharmacokinetic test also shows that the compounds of the invention have good pharmacokinetic absorption and obvious pharmacokinetic absorption effect. Compared with INCB024360, the compound of the invention has better pharmacokinetics properties when their pharmacodynamics are comparable or the pharmacodynamics of the compound of the invention is even higher than that of INCB024360. The compounds of the invention have great medicinal value and broad market prospect, which are expected to be developed to a new generation of immunosuppressants.

DETAILED DESCRIPTION

The following examples further describe the invention. However, these examples are only for illustrating the invention without limiting the scope of the invention.

Example 1

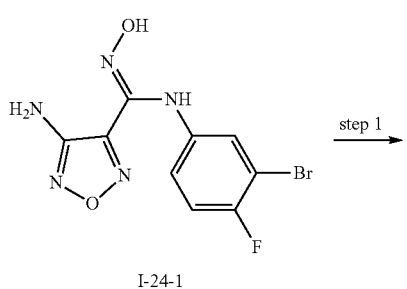

I-24-1

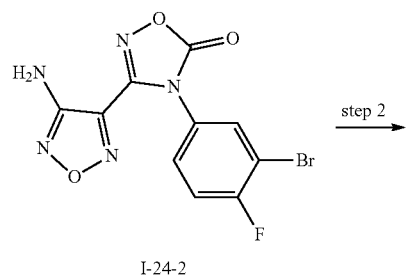

I-24-2

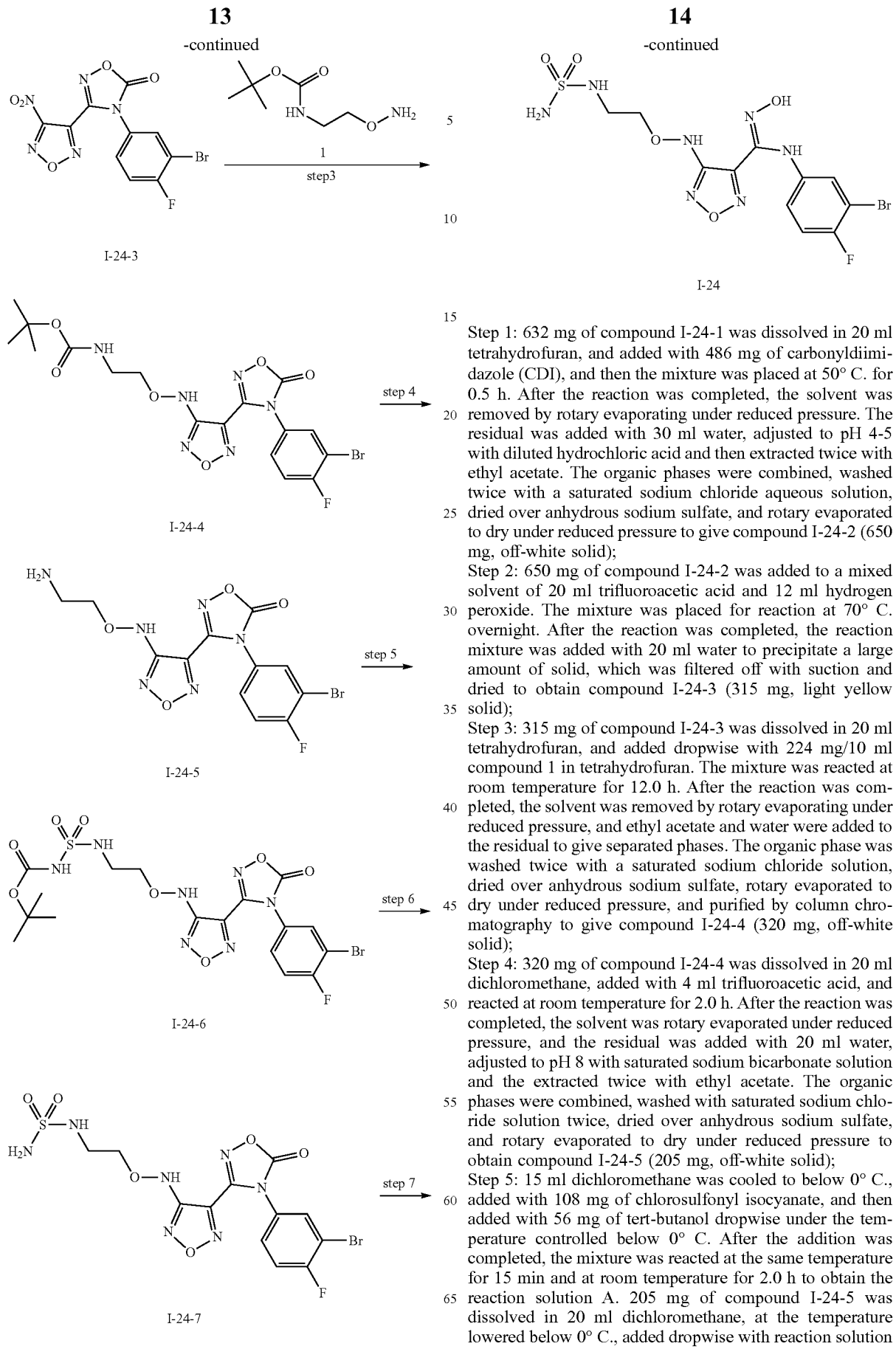

Step 1: 632 mg of compound I-24-1 was dissolved in 20 ml tetrahydrofuran, and added with 486 mg of carbonyldiimidazole (CDI), and then the mixture was placed at 50° C. for 0.5 h. After the reaction was completed, the solvent was removed by rotary evaporating under reduced pressure. The residual was added with 30 ml water, adjusted to pH 4-5 with diluted hydrochloric acid and then extracted twice with ethyl acetate. The organic phases were combined, washed twice with a saturated sodium chloride aqueous solution, dried over anhydrous sodium sulfate, and rotary evaporated to dry under reduced pressure to give compound I-24-2 (650 mg, off-white solid);

Step 2: 650 mg of compound I-24-2 was added to a mixed solvent of 20 ml trifluoroacetic acid and 12 ml hydrogen peroxide. The mixture was placed for reaction at 70° C. overnight. After the reaction was completed, the reaction mixture was added with 20 ml water to precipitate a large amount of solid, which was filtered off with suction and dried to obtain compound I-24-3 (315 mg, light yellow solid);

Step 3: 315 mg of compound I-24-3 was dissolved in 20 ml tetrahydrofuran, and added dropwise with 224 mg/10 ml compound 1 in tetrahydrofuran. The mixture was reacted at room temperature for 12.0 h. After the reaction was completed, the solvent was removed by rotary evaporating under reduced pressure, and ethyl acetate and water were added to the residual to give separated phases. The organic phase was washed twice with a saturated sodium chloride solution, dried over anhydrous sodium sulfate, rotary evaporated to dry under reduced pressure, and purified by column chromatography to give compound I-24-4 (320 mg, off-white solid);

Step 4: 320 mg of compound I-24-4 was dissolved in 20 ml dichloromethane, added with 4 ml trifluoroacetic acid, and reacted at room temperature for 2.0 h. After the reaction was completed, the solvent was rotary evaporated under reduced pressure, and the residual was added with 20 ml water, adjusted to pH 8 with saturated sodium bicarbonate solution and the extracted twice with ethyl acetate. The organic phases were combined, washed with saturated sodium chloride solution twice, dried over anhydrous sodium sulfate, and rotary evaporated to dry under reduced pressure to obtain compound I-24-5 (205 mg, off-white solid);

Step 5: 15 ml dichloromethane was cooled to below 0° C., added with 108 mg of chlorosulfonyl isocyanate, and then added with 56 mg of tert-butanol dropwise under the temperature controlled below 0° C. After the addition was completed, the mixture was reacted at the same temperature for 15 min and at room temperature for 2.0 h to obtain the reaction solution A. 205 mg of compound I-24-5 was dissolved in 20 ml dichloromethane, at the temperature lowered below 0° C., added dropwise with reaction solution A, then added dropwise with 155 mg of triethylamine, and reacted for 2.0 h. After the reaction was completed, the mixture was added with saturated sodium bicarbonate to quench the reaction and for liquid separation. The organic phase was washed twice with saturated sodium chloride solution, dried over anhydrous sodium sulfate, rotary evaporated to dry under reduced pressure, and purified by column chromatography to obtain compound I-24-6 (225 mg, off-white solid);

Step 6: 225 mg of compound I-24-6 was dissolved in 20 ml dichloromethane, added with 4 ml trifluoroacetic acid, and reacted at room temperature for 2.0 h. After the reaction was completed, the solvent was rotary evaporated under reduced pressure and the residual was added with 20 ml water, adjusted to pH 8 with saturated sodium bicarbonate, and extracted twice with ethyl acetate. Organic phases were combined, washed twice with saturated sodium chloride solution, dried over anhydrous sodium sulfate, and rotary evaporated to dry under reduced pressure to obtain compound I-24-7 (160 mg, off-white solid);

Step 7: 160 mg of compound I-24-7 was dissolved in 20 ml tetrahydrofuran, added with 1 ml 2.5M sodium hydroxide solution, and reacted at room temperature for 2.0 h. After the reaction was completed, saturated ammonium chloride solution and ethyl acetate were added to separate the liquid phases. The organic phase was washed twice with saturated sodium chloride solution, dried over anhydrous sodium sulfate, rotary evaporated to dry under reduced pressure and purified by column chromatography to obtain compound I-24 (18 mg, off-white solid, purity: 98.2%).

Example 2

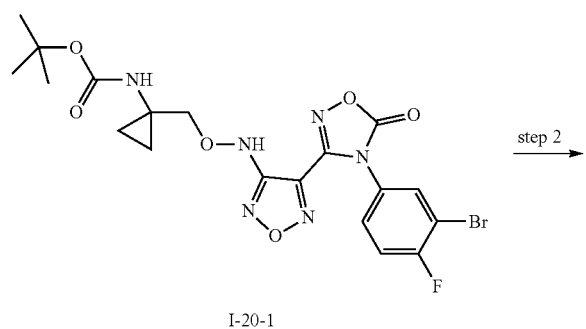

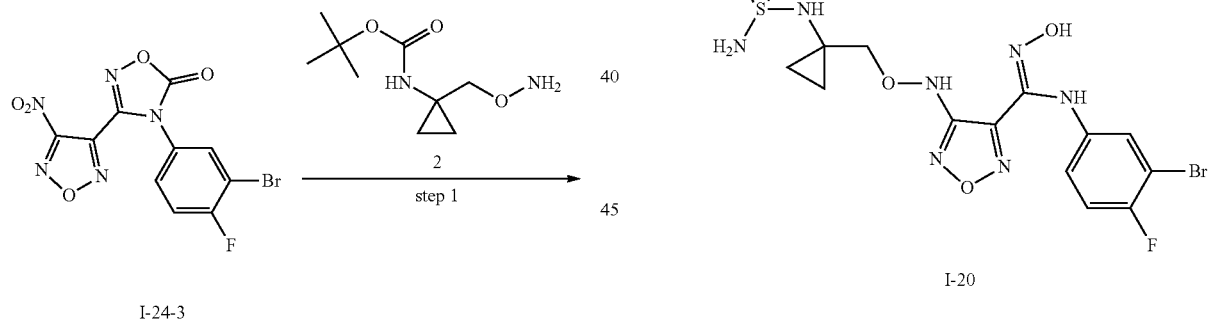

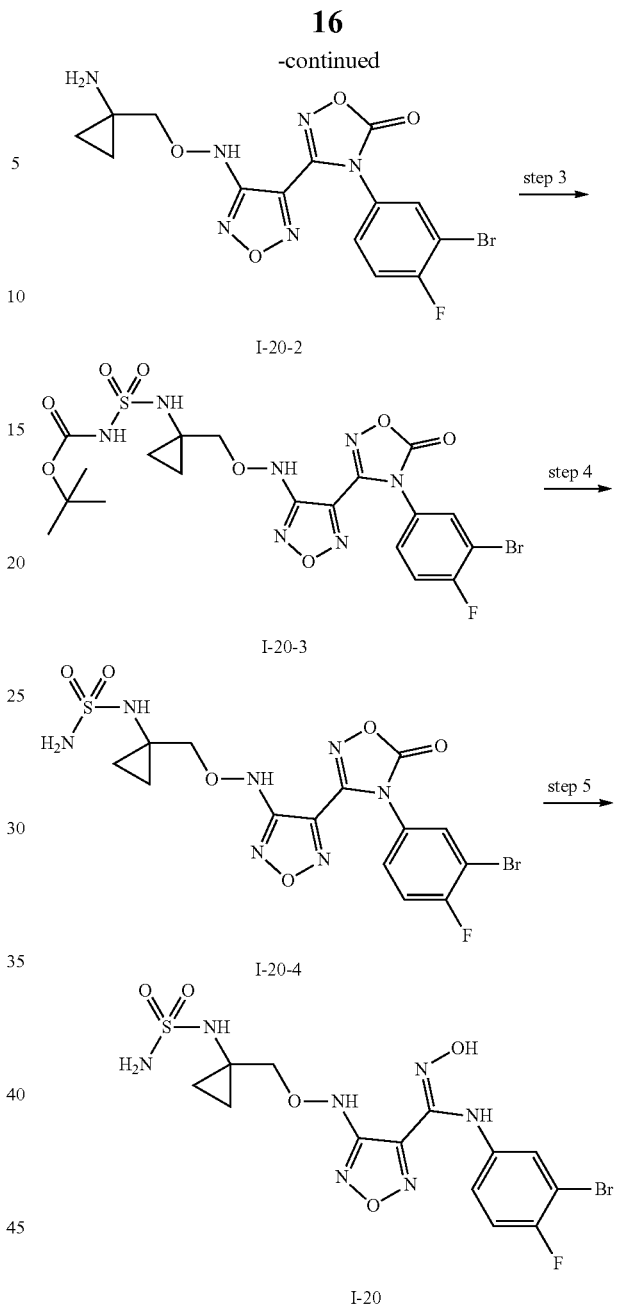

Step 1: 320 mg of compound I-24-3 was dissolved in 20 ml tetrahydrofuran, added dropwise with 262 mg/10 ml compound 2 in tetrahydrofuran, and reacted at room temperature for 6.0 h. After the reaction was completed, the solvent was rotary evaporated under reduced pressure; ethyl acetate and water were added to separate liquid phases. The organic phase was washed twice with saturated sodium chloride solution, dried over anhydrous sodium sulfate, and rotary evaporated to dry under reduced pressure, and purified by column chromatography to obtain compound I-20-1 (364 mg, off-white solid);

Step 2: 364 mg of compound I-20-1 was dissolved in 20 ml dichloromethane, added with 4 ml trifluoroacetic acid, and reacted at room temperature for 2.0 h. After the reaction was complete, the solvent was rotary evaporated under reduced pressure, and the residual was added with 20 ml water, adjusted to pH 8 with saturated sodium bicarbonate, and extracted with ethyl acetate twice. The organic phases were combined, washed twice with saturated sodium chloride solution, dried over anhydrous sodium sulfate, and rotary evaporated to dry under reduced pressure to obtain compound I-20-2 (235 mg, off-white solid);

Step 3: 15 ml dichloromethane was cooled to below 0° C., added with 118 mg of chlorosulfonyl isocyanate, and then added dropwise with 60 mg of tert-butanol under the temperature controlled below 0° C. After the addition was completed, the mixture was reacted at the same temperature for 15 min and at room temperature for 2.0 h to obtain the reaction solution A.

235 mg of compound I-20-2 was dissolved in 20 ml dichloromethane, the temperature was reduced below 0° C., added dropwise with reaction solution A, then added dropwise with 166 mg of triethylamine, and reacted for 2.0 h. After the reaction was completed, the mixture was added with saturated sodium bicarbonate to quench the reaction and for liquid separation. The organic phase was washed twice with saturated sodium chloride solution, dried over anhydrous sodium sulfate, rotary evaporated to dry under reduced pressure, and purified by column chromatography to obtain compound I-20-3 (260 mg, off-white solid);

Step 4: 260 mg of compound I-20-3 was dissolved in 20 ml dichloromethane, added with 4 ml trifluoroacetic acid, and reacted at room temperature for 2.0 h. After the reaction was completed, the solvent was rotary evaporated under reduced pressure and the residual was added with 20 ml water, adjusted to pH 8 with saturated sodium bicarbonate, and extracted twice with ethyl acetate. Organic phases were combined, washed twice with saturated sodium chloride solution, dried over anhydrous sodium sulfate, and rotary evaporated to dry under reduced pressure to obtain compound I-20-4 (184 mg, off-white solid);

Step 5: 184 mg of compound I-20-4 was dissolved in 20 ml tetrahydrofuran, added with 1 ml 2.5M sodium hydroxide solution, and reacted at room temperature for 2.0 h. After the reaction was completed, saturated ammonium chloride solution and ethyl acetate were added to separate the liquid phases. The organic phase was washed twice with saturated sodium chloride solution, dried over anhydrous sodium sulfate, rotary evaporated to dry under reduced pressure and purified by column chromatography to obtain compound I-20 (25 mg, off-white solid, purity: 97.8%).

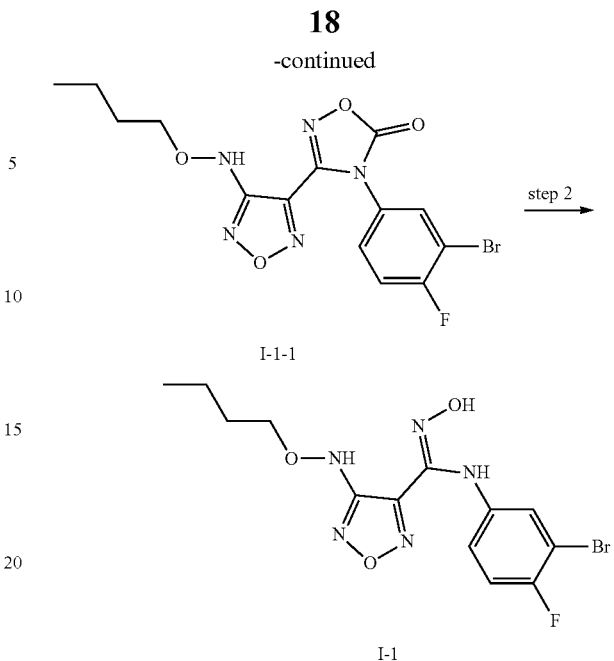

Step 1: 200 mg of compound I-24-3 was dissolved in 20 ml tetrahydrofuran, and added dropwise with 97 mg/10 ml compound 3 in tetrahydrofuran. The mixture was reacted at room temperature for 6.0 h. After the reaction was completed, the solvent was rotary evaporated under reduced pressure, and ethyl acetate and water were added to the residual to give separated phases. The organic phase was washed twice with a saturated sodium chloride solution, dried over anhydrous sodium sulfate, rotary evaporated to dry under reduced pressure, and purified by column chromatography to give compound I-1-1 (180 mg, off-white solid);

Step 2: 180 mg of compound I-1-1 was dissolved in 20 ml tetrahydrofuran, added with 1 ml 2.5M sodium hydroxide solution, and reacted at room temperature for 2.0 h. After the reaction was completed, saturated ammonium chloride solution and ethyl acetate were added to separate the liquid phases. The organic phase was washed twice with saturated sodium chloride solution, dried over anhydrous sodium sulfate, rotary evaporated to dry under reduced pressure and purified by column chromatography to obtain compound I-1 (15 mg, off-white solid, purity: 96.4%).

Example 3

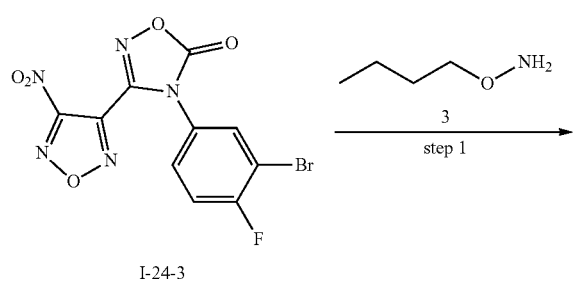

Example 4

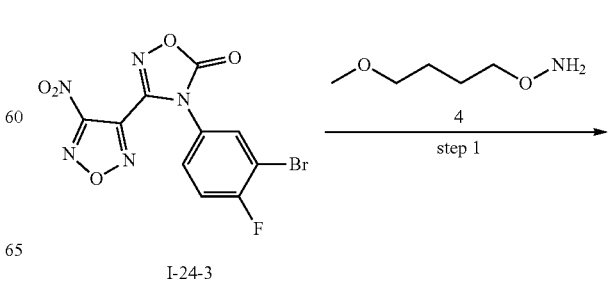

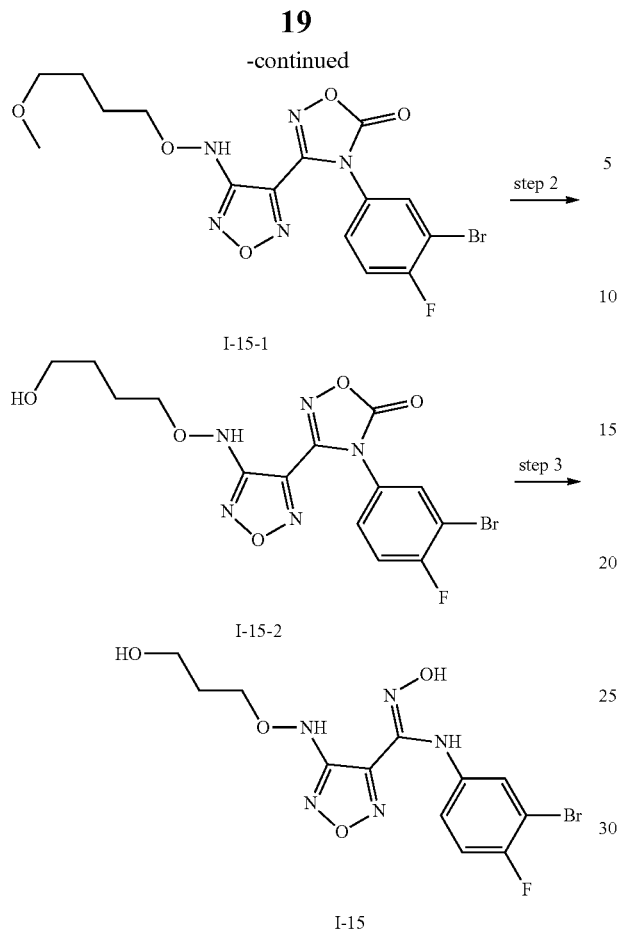

I-15-1

I-15-2

I-15

Step 1: 200 mg of compound I-24-3 was dissolved in 20 ml tetrahydrofuran, added dropwise with 128 mg/10 ml compound 4 in tetrahydrofuran, and reacted at room temperature for 6.0 h. After the reaction was completed, the solvent was rotary evaporated under reduced pressure; ethyl acetate and water were added to separate liquid phases. The organic phase was washed twice with saturated sodium chloride solution, dried over anhydrous sodium sulfate, and rotary evaporated to dry under reduced pressure, and purified by column chromatography to obtain compound I-15-1 (196 mg, off-white solid);

Step 2: 196 mg of compound I-15-1 was dissolved in 20 ml dichloromethane, cooled to −70° C., slowly added dropwise with 220 mg of boron tribromide, and slowly warmed to −10° C. for 0.5 h after the addition. After the reaction was completed, the mixture was kept at room temperature, added with saturated sodium bicarbonate to quench the reaction, and extracted with dichloromethane. The organic phase was washed twice with saturated sodium chloride solution, dried over anhydrous sodium sulfate, rotary evaporated to dry, and purified by column chromatography to obtain compound I-15-2 (120 mg, oil);

Step 3: 120 mg of compound I-15-2 was dissolved in 20 ml tetrahydrofuran, added with 1 ml 2.5M sodium hydroxide solution, and reacted at room temperature for 2.0 h. After the reaction was completed, added with saturated ammonium chloride solution and ethyl acetate to separate the liquid phases. The organic phase was washed twice with saturated sodium chloride solution, dried over anhydrous sodium sulfate, rotary evaporated to dry under reduced pressure, and purified by column chromatography to obtain compound I-15 (11 mg, off-white solid, purity: 96.5%);

Example 5

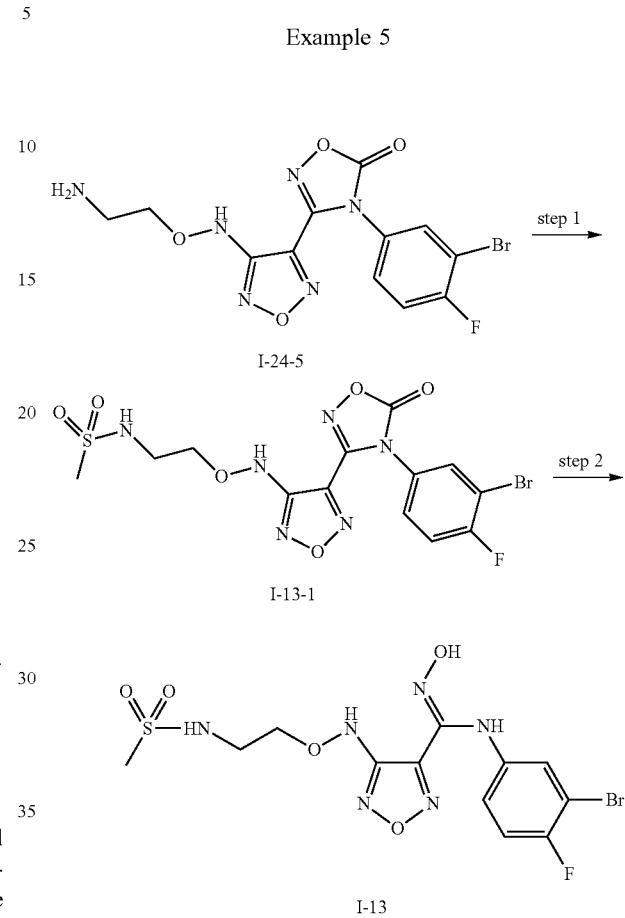

I-24-5

I-13-1

I-13

Step 1: 200 mg of compound I-24-5 was dissolved in 20 ml dichloromethane, and added with 100 mg of triethylamine. The mixture was placed at 0° C., added with 115 mg of methanesulfonyl chloride dropwise and kept reacting for 2.0 h after the addition was completed. After the reaction was completed, the reaction mixture was added with water, and adjusted to pH 4-5 with dilute hydrochloric acid. The separated organic phase was washed twice with saturated sodium chloride solution, dried over anhydrous sodium sulfate, and rotary evaporated to dry under reduced pressure to obtain crude compound I-13-1 (180 mg, oil), which was used directly in the next step;

Step 2: 180 mg of compound I-13-1 was dissolved in 20 ml tetrahydrofuran, added with 1 ml 2.5M sodium hydroxide solution, and reacted at room temperature for 2.0 h. After the reaction was completed, the mixture was added with saturated ammonium chloride solution and ethyl acetate to separate the liquid phases. The organic phase was washed twice with saturated sodium chloride solution, dried over anhydrous sodium sulfate, rotary evaporated to dry under reduced pressure, and purified by column chromatography to obtain compound I-13 (19 mg, off-white solid, purity: 96.8%);

Example 6

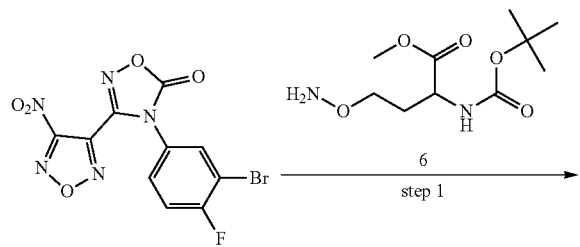

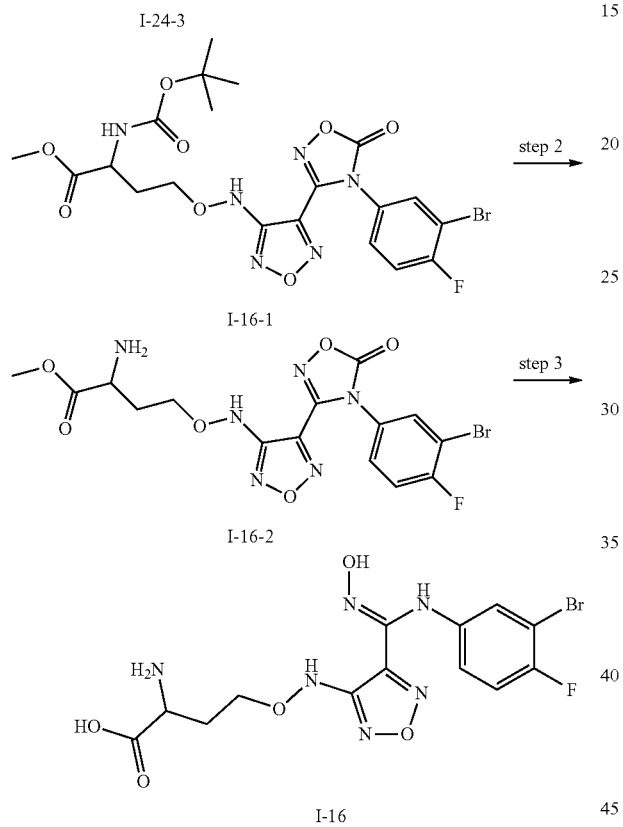

Step 1: 370 mg of compound I-24-3 was dissolved in 20 ml tetrahydrofuran, added dropwise with 496 mg/10 ml compound 6 in tetrahydrofuran, and reacted at room temperature for 6.0 h. After the reaction was completed, the solvent was rotary evaporated under reduced pressure; ethyl acetate and water were added to separate liquid phases. The organic phase was washed twice with saturated sodium chloride solution, dried over anhydrous sodium sulfate, and rotary evaporated to dry under reduced pressure, and purified by column chromatography to obtain compound I-16-1 (430 mg, off-white solid);

Step 2: 430 mg of compound I-16-1 was dissolved in 20 ml dichloromethane, added with 4 ml trifluoroacetic acid, and reacted at room temperature for 2.0 h. After the reaction was complete, the solvent was rotary evaporated under reduced pressure, and the residual was added with 20 ml water, adjusted to about pH 8 with saturated sodium bicarbonate, and extracted with ethyl acetate twice. The organic phases were combined, washed twice with saturated sodium chloride solution, dried over anhydrous sodium sulfate, and rotary evaporated to dry under reduced pressure to obtain compound I-16-2 (284 mg, off-white solid);

Step 3: 284 mg of compound I-16-2 was dissolved in 20 ml tetrahydrofuran, added with 1 ml 2.5M sodium hydroxide solution, and reacted at room temperature for 2.0 h. After the reaction was completed, saturated ammonium chloride solution and ethyl acetate were added to separate the liquid phases. The organic phase was washed twice with saturated sodium chloride solution, dried over anhydrous sodium sulfate, rotary evaporated to dry under reduced pressure and purified by column chromatography to obtain compound I-16 (20 mg, off-white solid, purity: 98.5%).

Example 7

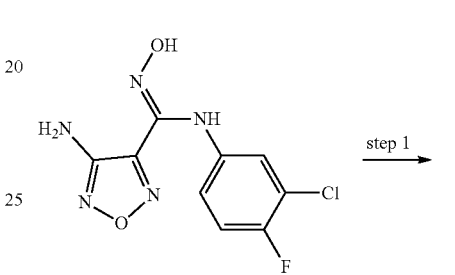

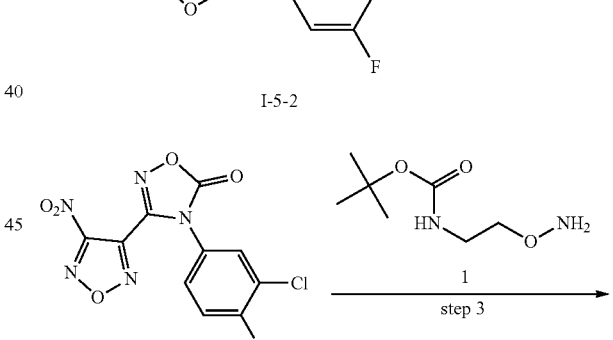

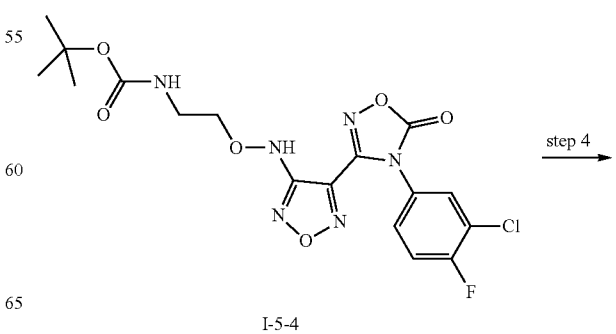

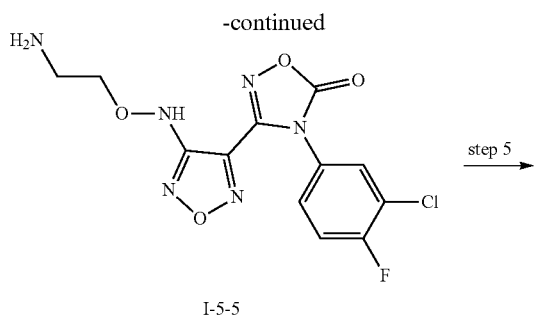

I-5-5

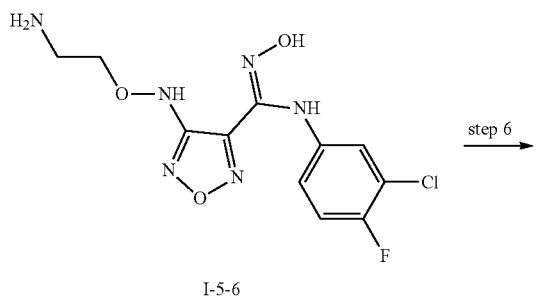

I-5-6

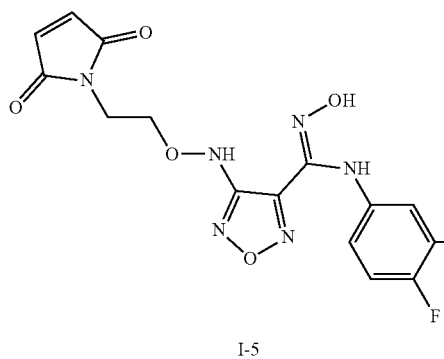

I-5

Step 1: 542 mg of compound I-5-1 was dissolved in 20 ml tetrahydrofuran, and added with 486 mg of carbonyldiimidazole (CDI), and then the mixture was placed at 50° C. for 0.5 h. After the reaction was completed, the solvent was removed by rotary evaporating under vacuum. The residual was added with 30 ml water, adjusted to pH 4-5 with diluted hydrochloric acid and then extracted twice with ethyl acetate. The organic phases were combined, washed twice with a saturated sodium chloride aqueous solution, dried over anhydrous sodium sulfate and rotary evaporated to dry under reduced pressure to give compound I-5-2 (564 mg, off-white solid);

Step 2: 564 mg of compound I-5-2 was added to a mixed solvent of 20 ml trifluoroacetic acid and 12 ml hydrogen peroxide. The mixture was placed for reaction at 70° C. overnight. After the reaction was completed, the reaction mixture was added with 20 ml water to precipitate a large amount of solid, which was filtered off with suction and dried to obtain compound I-5-3 (402 mg, light yellow solid);

Step 3: 402 mg of compound I-5-3 was dissolved in 20 ml tetrahydrofuran, and added dropwise with 324 mg/10 ml compound 1 in tetrahydrofuran. The mixture was reacted at room temperature for 12.0 h. After the reaction was completed, the solvent was rotary evaporated under reduced pressure, and ethyl acetate and water were added to the residual to give separated phases. The organic phase was washed twice with a saturated sodium chloride solution, dried over anhydrous sodium sulfate, rotary evaporated to dry under reduced pressure, and purified by column chromatography to give compound I-5-4 (465 mg, off-white solid);

Step 4: 465 mg of compound I-5-4 was dissolved in 20 ml dichloromethane, added with 4 ml trifluoroacetic acid, and reacted at room temperature for 2.0 h. After the reaction was completed, the solvent was rotary evaporated under reduced pressure, and the residual was added with 20 ml water, adjusted to pH 8 with saturated sodium bicarbonate and the extracted twice with ethyl acetate. The organic phases were combined, washed with saturated sodium chloride solution twice, dried over anhydrous sodium sulfate, and rotary evaporated to dry under reduced pressure to obtain compound I-5-5 (308 mg, off-white solid);

Step 5: 308 mg of compound I-5-4 was dissolved in 20 ml tetrahydrofuran, added with 1 ml 2.5M sodium hydroxide solution, and reacted at room temperature for 2.0 h. After the reaction was completed, saturated ammonium chloride solution and ethyl acetate were added to separate the liquid phases. The organic phase was washed twice with saturated sodium chloride solution, dried over anhydrous sodium sulfate, rotary evaporated to dry under reduced pressure and purified by column chromatography to obtain compound I-7-5 (256 mg, off-white solid), which was used directly in the next step.

Step 6: 256 mg of compound I-5-5 was dissolved in 20 ml ethanol, added with 115 mg of maleic anhydride, and reacted at reflux for 6.0 h. After the reaction was completed, the solvent was rotary evaporated under reduced pressure and the residual was added with water and ethyl acetate to separate liquid phases. The organic phase was washed twice with a saturated sodium chloride solution, dried over anhydrous sodium sulfate, rotary evaporated to dry under reduced pressure, and purified by column chromatography to obtain compound I-5 (13 mg, off-white solid, purity: 97.2%).

Example 8

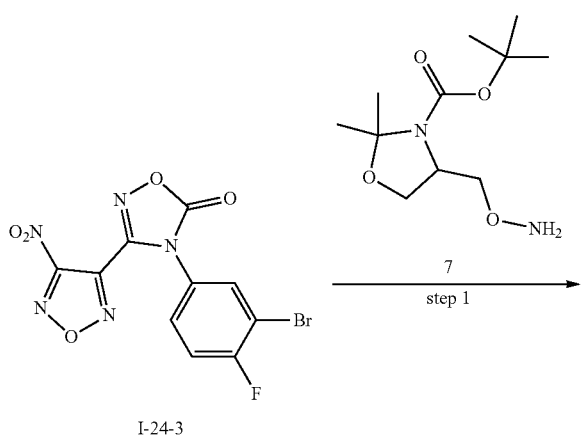

I-24-3

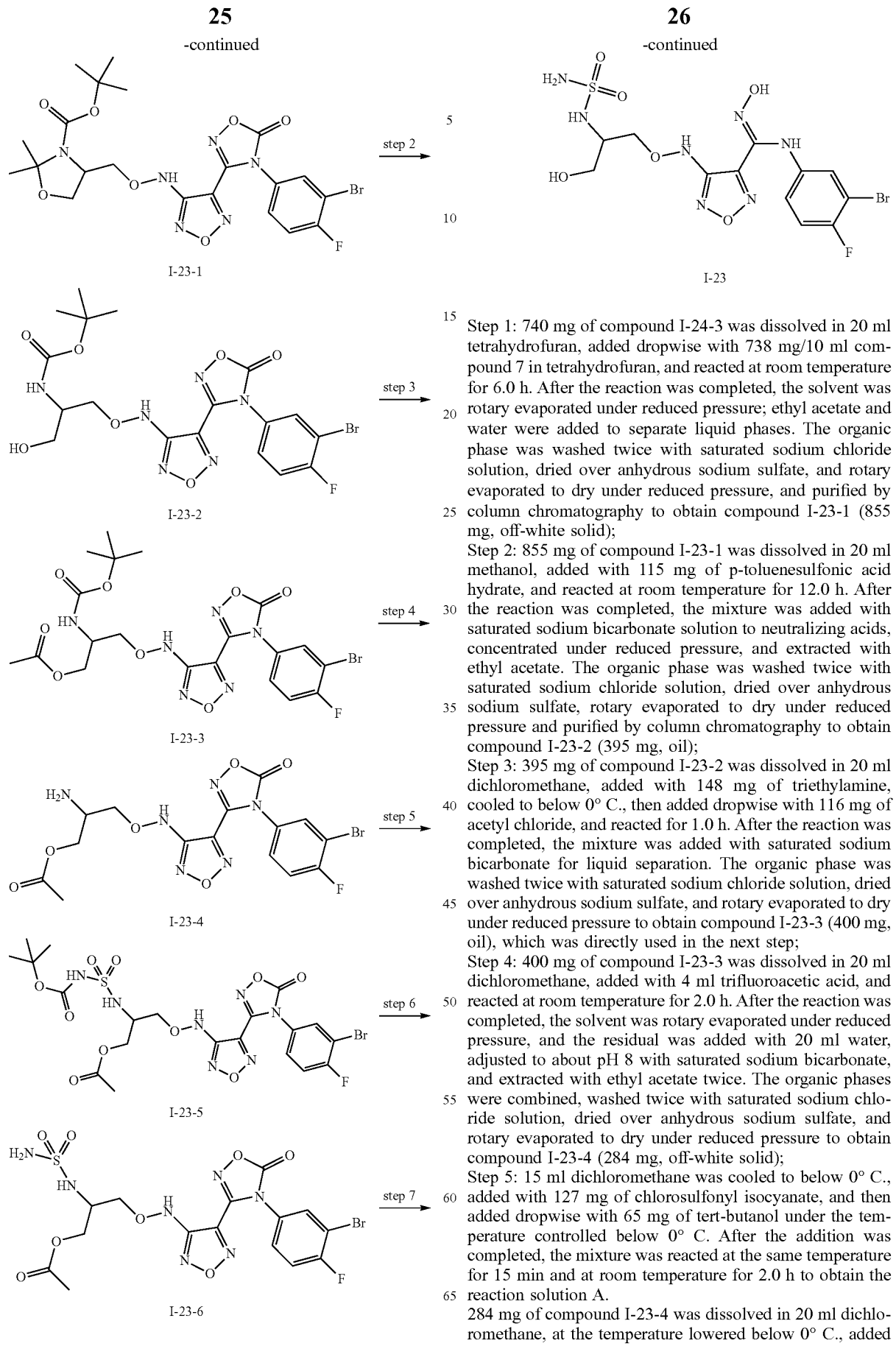

Step 1: 740 mg of compound I-24-3 was dissolved in 20 ml tetrahydrofuran, added dropwise with 738 mg/10 ml compound 7 in tetrahydrofuran, and reacted at room temperature for 6.0 h. After the reaction was completed, the solvent was rotary evaporated under reduced pressure; ethyl acetate and water were added to separate liquid phases. The organic phase was washed twice with saturated sodium chloride solution, dried over anhydrous sodium sulfate, and rotary evaporated to dry under reduced pressure, and purified by column chromatography to obtain compound I-23-1 (855 mg, off-white solid);

Step 2: 855 mg of compound I-23-1 was dissolved in 20 ml methanol, added with 115 mg of p-toluenesulfonic acid hydrate, and reacted at room temperature for 12.0 h. After the reaction was completed, the mixture was added with saturated sodium bicarbonate solution to neutralizing acids, concentrated under reduced pressure, and extracted with ethyl acetate. The organic phase was washed twice with saturated sodium chloride solution, dried over anhydrous sodium sulfate, rotary evaporated to dry under reduced pressure and purified by column chromatography to obtain compound I-23-2 (395 mg, oil);

Step 3: 395 mg of compound I-23-2 was dissolved in 20 ml dichloromethane, added with 148 mg of triethylamine, cooled to below 0° C., then added dropwise with 116 mg of acetyl chloride, and reacted for 1.0 h. After the reaction was completed, the mixture was added with saturated sodium bicarbonate for liquid separation. The organic phase was washed twice with saturated sodium chloride solution, dried over anhydrous sodium sulfate, and rotary evaporated to dry under reduced pressure to obtain compound I-23-3 (400 mg, oil), which was directly used in the next step;

Step 4: 400 mg of compound I-23-3 was dissolved in 20 ml dichloromethane, added with 4 ml trifluoroacetic acid, and reacted at room temperature for 2.0 h. After the reaction was completed, the solvent was rotary evaporated under reduced pressure, and the residual was added with 20 ml water, adjusted to about pH 8 with saturated sodium bicarbonate, and extracted with ethyl acetate twice. The organic phases were combined, washed twice with saturated sodium chloride solution, dried over anhydrous sodium sulfate, and rotary evaporated to dry under reduced pressure to obtain compound I-23-4 (284 mg, off-white solid);

Step 5: 15 ml dichloromethane was cooled to below 0° C., added with 127 mg of chlorosulfonyl isocyanate, and then added dropwise with 65 mg of tert-butanol under the temperature controlled below 0° C. After the addition was completed, the mixture was reacted at the same temperature for 15 min and at room temperature for 2.0 h to obtain the reaction solution A.

284 mg of compound I-23-4 was dissolved in 20 ml dichloromethane, at the temperature lowered below 0° C., added dropwise with reaction solution A, then added dropwise with 240 mg of triethylamine, and reacted for 2.0 h. After the reaction was completed, the mixture was added with saturated sodium bicarbonate to quench the reaction and for liquid separation. The organic phase was washed twice with saturated sodium chloride solution, dried over anhydrous sodium sulfate, rotary evaporated to dry under reduced pressure, and purified by column chromatography to obtain compound I-23-5 (293 mg, off-white solid);

Step 6: 293 mg of compound I-23-5 was dissolved in 20 ml dichloromethane, added with 4 ml trifluoroacetic acid, and reacted at room temperature for 2.0 h. After the reaction was completed, the solvent was rotary evaporated under reduced pressure and the residual was added with 20 ml water, adjusted to pH 8 with saturated sodium bicarbonate, and extracted twice with ethyl acetate. Organic phases were combined, washed twice with saturated sodium chloride solution, dried over anhydrous sodium sulfate, and rotary evaporated to dry under reduced pressure to obtain compound I-23-6 (198 mg, off-white solid);

Step 7: 198 mg of compound I-23-6 was dissolved in 20 ml methanol, added with 248 mg of potassium carbonate, and reacted at 50° C. for 2.0 h. After the reaction was completed, the mixture was added with saturated ammonium chloride solution and ethyl acetate to separate the liquid phases. The organic phase was washed twice with saturated sodium chloride solution, dried over anhydrous sodium sulfate, rotary evaporated to dry under reduced pressure, and purified by column chromatography to obtain compound I-23 (18 mg, off-white solid, purity: 97.6%).

Example 9

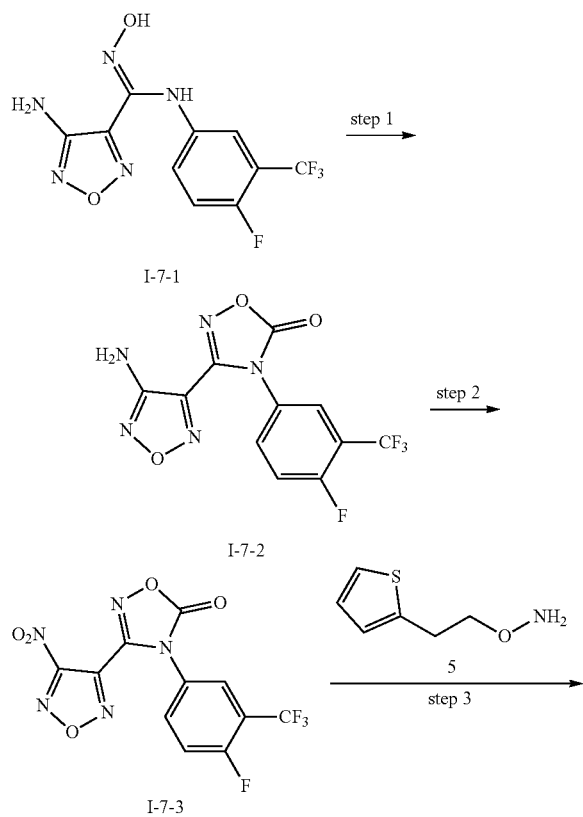

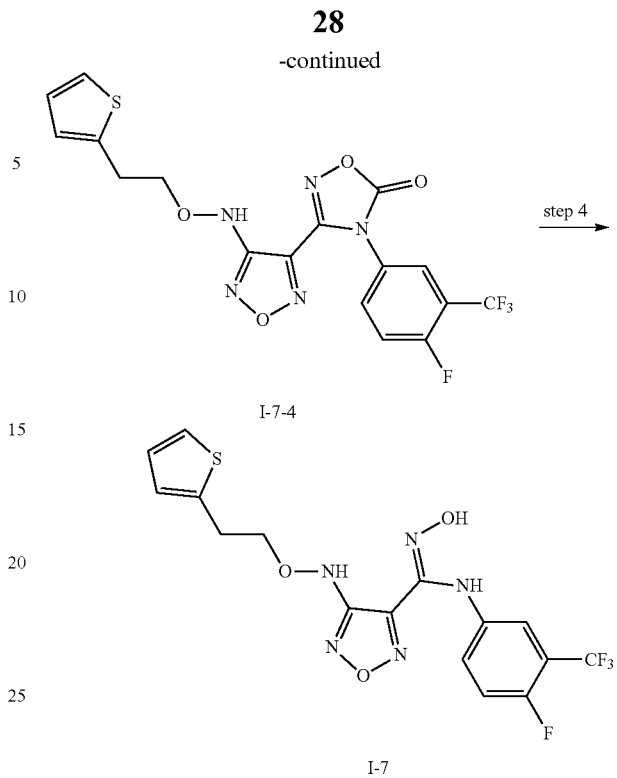

Step 1: 710 mg of compound I-7-1 was dissolved in 20 ml tetrahydrofuran, and added with 486 mg of CDI, and then the mixture was placed at 50° C. for 0.5 h. After the reaction was completed, the solvent was removed by rotary evaporating under vacuum. The residual was added with 30 ml water, adjusted to pH4-5 with diluted hydrochloric acid and then extracted twice with ethyl acetate. The organic phases were combined, washed twice with a saturated sodium chloride aqueous solution, dried over anhydrous sodium sulfate and rotary evaporated to dry under reduced pressure to give compound I-7-2 (610 mg, off-white solid);

Step 2: 610 mg of compound I-7-2 was added to a mixed solvent of 20 ml trifluoroacetic acid and 12 ml hydrogen peroxide. The mixture was placed for reaction at 70° C. overnight. After the reaction was completed, the reaction mixture was added with 20 ml water to precipitate a large amount of solid, which was filtered and dried to obtain compound I-7-3 (365 mg, light yellow solid);

Step 3: 365 mg of compound I-7-3 was dissolved in 20 ml tetrahydrofuran, and added dropwise with 215 mg/10 ml compound 5 in tetrahydrofuran. The mixture was reacted at room temperature for 12.0 h. After the reaction was completed, the solvent was rotary evaporated under reduced pressure, and ethyl acetate and water were added to the residual to give separated phases. The organic phase was washed twice with a saturated sodium chloride solution, dried over anhydrous sodium sulfate, rotary evaporated to dry under reduced pressure, and purified by column chromatography to give compound I-7-4 (375 mg, off-white solid);

Step 4: 375 mg of compound I-7-4 was dissolved in 20 ml tetrahydrofuran, added with 1 ml 2.5M sodium hydroxide solution, and reacted at room temperature for 2.0 h. After the reaction was completed, saturated ammonium chloride solution and ethyl acetate were added to separate the liquid phases. The organic phase was washed twice with saturated sodium chloride solution, dried over anhydrous sodium sulfate, rotary evaporated to dry under reduced pressure and purified by column chromatography to obtain compound I-7 (26 mg, off-white solid, purity: 97.6%).

Example 10

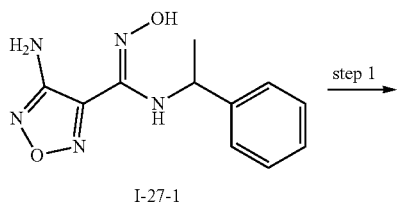

Step 1: 494 mg of compound I-27-1 was dissolved in 20 ml tetrahydrofuran, and added with 486 mg of CDI, and then the mixture was placed at 50° C. for 0.5 h. After the reaction was completed, the solvent was removed by rotary evaporating under vacuum. The residual was added with 30 ml water, adjusted to pH4-5 with diluted hydrochloric acid and then extracted twice with ethyl acetate. The organic phases were combined, washed twice with a saturated sodium chloride aqueous solution, dried over anhydrous sodium sulfate and rotary evaporated to dry under reduced pressure to give compound I-27-2 (518 mg, off-white solid);

Step 2: 518 mg of compound I-27-2 was added to a mixed solvent of 20 ml trifluoroacetic acid and 12 ml hydrogen peroxide. The mixture was placed for reaction at 70° C. overnight. After the reaction was completed, the reaction mixture was added with 20 ml water to precipitate a large amount of solid, which was filtered and dried to obtain compound I-27-3 (345 mg, light yellow solid);

Step 3: 345 mg of compound I-27-3 was dissolved in 20 ml tetrahydrofuran, and added dropwise with 300 mg/10 ml compound 1 in tetrahydrofuran. The mixture was reacted at room temperature for 12.0 h. After the reaction was completed, the solvent was rotary evaporated under reduced pressure, and ethyl acetate and water were added to the residual to give separated phases. The organic phase was washed twice with a saturated sodium chloride solution, dried over anhydrous sodium sulfate, rotary evaporated to dry under reduced pressure, and purified by column chromatography to give compound I-27-4 (334 mg, off-white solid);

Step 4: 334 mg of compound I-27-4 was dissolved in 20 ml dichloromethane, added with 4 ml trifluoroacetic acid, and reacted at room temperature for 2.0 h. After the reaction was completed, the solvent was rotary evaporated under reduced pressure, and the residual was added with 20 ml water, adjusted to about pH8 with saturated sodium bicarbonate, and extracted with ethyl acetate twice. The organic phases were combined, washed twice with saturated sodium chloride solution, dried over anhydrous sodium sulfate, and rotary evaporated to dry under reduced pressure to obtain compound I-27-5 (225 mg, off-white solid);

Step 5: 15 ml dichloromethane was cooled to below 0° C., added with 150 mg of chlorosulfonyl isocyanate, and then added dropwise with 73 mg of tert-butanol under the temperature controlled below 0° C. After the addition was completed, the mixture was reacted at the same temperature for 15 min and at room temperature for 2.0 h to obtain the reaction solution A. 225 mg of compound I-27-5 was dissolved in 20 ml dichloromethane, at the temperature lowered below 0° C., added dropwise with reaction solution A, then added dropwise with 205 mg of triethylamine, and reacted for 2.0 h. After the reaction was completed, the mixture was added with saturated sodium bicarbonate to quench the reaction and for liquid separation. The organic phase was washed twice with saturated sodium chloride solution, dried over anhydrous sodium sulfate, rotary evaporated to dry under reduced pressure, and purified by column chromatography to obtain compound I-27-6 (263 mg, off-white solid);

Step 6: 263 mg of compound I-27-6 was dissolved in 20 ml dichloromethane, added with 4 ml trifluoroacetic acid, and reacted at room temperature for 2.0 h. After the reaction was completed, the solvent was rotary evaporated under reduced pressure and the residual was added with 20 ml water, adjusted to pH 8 with saturated sodium bicarbonate, and extracted twice with ethyl acetate. Organic phases were combined, washed twice with saturated sodium chloride solution, dried over anhydrous sodium sulfate, and rotary evaporated to dry under reduced pressure to obtain compound I-27-7 (180 mg, off-white solid);

Step 4: 180 mg of compound I-27-7 was dissolved in 20 ml tetrahydrofuran, added with 1 ml 2.5M sodium hydroxide solution, and reacted at room temperature for 2.0 h. After the reaction was completed, saturated ammonium chloride solution and ethyl acetate were added to separate the liquid phases. The organic phase was washed twice with saturated sodium chloride solution, dried over anhydrous sodium sulfate, rotary evaporated to dry under reduced pressure and purified by column chromatography to obtain compound I-27 (22 mg, off-white solid, purity: 96.9%).

Example 11

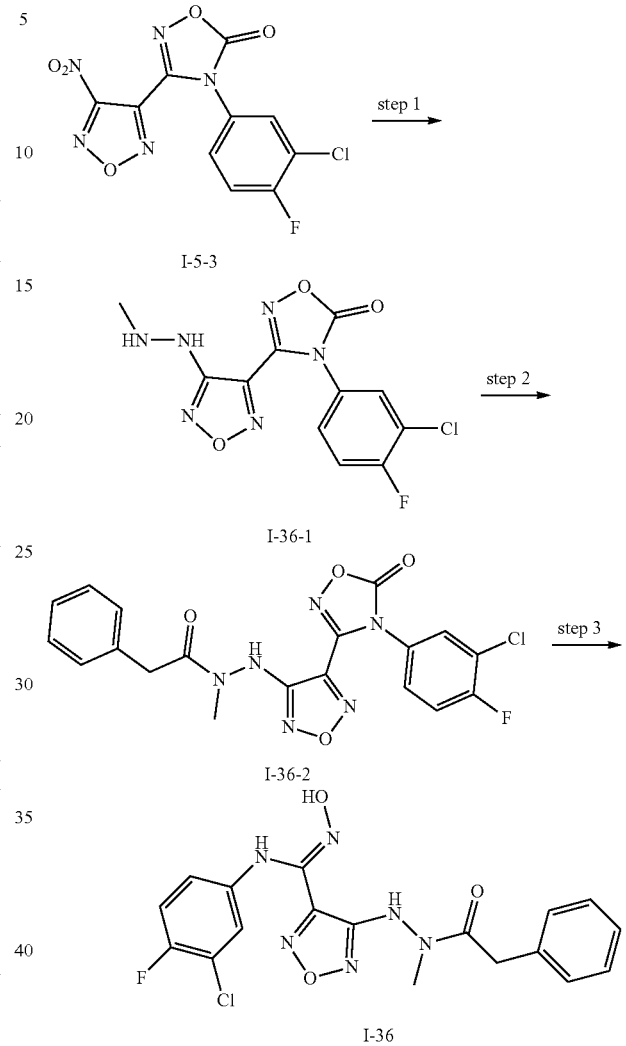

Step 1: 981 mg of compound I-5 was dissolved in 20 ml tetrahydrofuran, added dropwise with 10 ml solution of 20% methylhydrazine in tetrahydrofuran, and reacted at room temperature for 2.0 h. After the reaction was completed, the solvent was rotary evaporated under reduced pressure; ethyl acetate and water were added to separate the liquid phases. The organic phase was washed twice with saturated sodium chloride solution, dried over anhydrous sodium sulfate, rotary evaporated to dry and purified by column chromatography under reduced pressure to obtain compound I-36-1 (780 mg, off-white solid);

Step 2: 780 mg of compound I-36-1 was dissolved in 20 ml tetrahydrofuran, added dropwise with a solution of 405 mg of phenylacetyl chloride in 5 ml tetrahydrofuran, then added 263 mg of triethylamine, and reacted at room temperature for 0.5 h. After the reaction was completed, the solvent was rotary evaporated under reduced pressure, and the residual was added with 30 ml water, and extracted twice with ethyl acetate. The organic phases were combined, washed twice with saturated aqueous sodium chloride solution, dried over anhydrous sodium sulfate, and rotary evaporated to dry under reduced pressure to give compound I-36-2 (818 mg, off-white solid);

Step 3: 818 mg of compound I-36-2 was dissolved in 20 ml tetrahydrofuran, added with 1 ml 2.5M sodium hydroxide solution, and reacted at room temperature for 2.0 h. After the reaction was completed, saturated ammonium chloride solution and ethyl acetate were added to separate the liquid phases. The organic phase was washed twice with saturated sodium chloride solution, dried over anhydrous sodium sulfate, rotary evaporated to dry under reduced pressure and purified by column chromatography to obtain compound I-36 (38 mg, off-white solid, purity: 98.9%).

Example 12

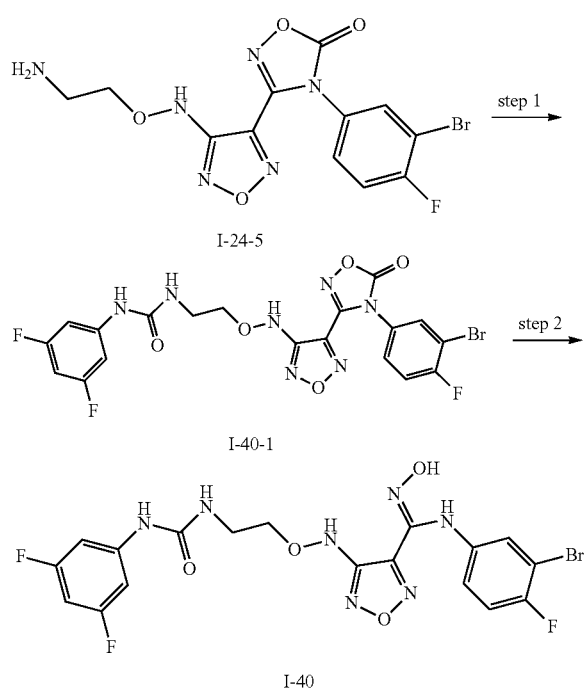

Step 1: 401 mg of compound I-24-5, 198 mg of 3,5-difluorobenzene isocyanate and 200 mg of triethylamine were dissolved in 10 ml DMF, and reacted overnight at room temperature. After the reaction was completed, the mixture was added with 50 ml water and then extracted twice with addition of ethyl acetate. The organic phases were combined, washed twice with saturated aqueous sodium chloride solution, dried over anhydrous sodium sulfate, rotary evaporated to dry under reduced pressure, and purified by column chromatography to obtain compound I-40-1 (283 mg, off-white solid);

Step 2: 283 mg of compound I-40-1 was completely dissolved in 20 ml tetrahydrofuran, added with 1 ml 2.5M sodium hydroxide solution, and reacted at room temperature for 2.0 h. After the reaction was completed, saturated ammonium chloride solution and ethyl acetate were added to separate the liquid phases. The organic phase was washed twice with saturated sodium chloride solution, dried over anhydrous sodium sulfate, rotary evaporated to dry under reduced pressure and purified by column chromatography to obtain compound I-40 (12 mg, off-white solid, purity: 95.8%).

With reference to the above examples of compound preparation methods, the following compounds were prepared through a series of reactions under suitable solvents and reaction temperatures. NMR and mass spectrometry were tested for compounds including but not limited to those shown in the table below.

| Compound structures and numbers | MS | $^1$H NMR |
|---|---|---|
| 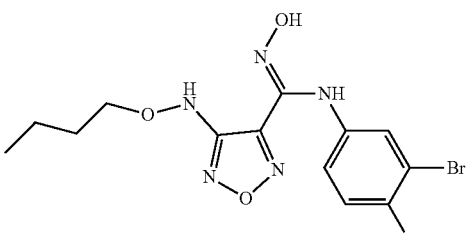<br>I-1 | [M + H]$^+$ = 389.0 | 1H NMR (400 MHz, d6-DMSO): 11.25 (s, 1H), 9.08 (s, 1H), 7.53-7.51 (m, 2H), 7.10-7.06 (m, 1H), 6.82 (s, 1H), 2.02 (s, 2H), 1.52-1.50 (m, 4H), 1.23-1.20 (dd, 3H) ppm. |
| 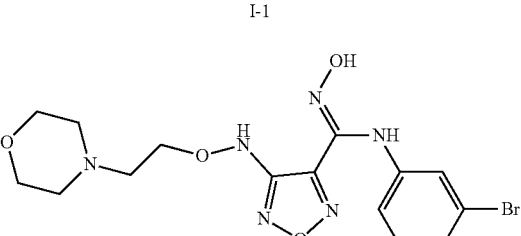<br>I-2 | [M + H]$^+$ = 446.2 | 1H NMR (400 MHz, d6-DMSO): 10.93 (s, 1H), 9.02 (s, 1H), 7.15-7.09 (m, 1H), 6.99-6.95 (m, 2H), 6.45 (s, 1H), 1.82-1.79 (m, 2H), 1.75-1.73 (m, 2H), 1.62-1.60 (m, 4H), 1.55-1.53 (m, 4H) ppm. |

-continued
| Compound structures and numbers | MS | ¹H NMR |
|---|---|---|
| 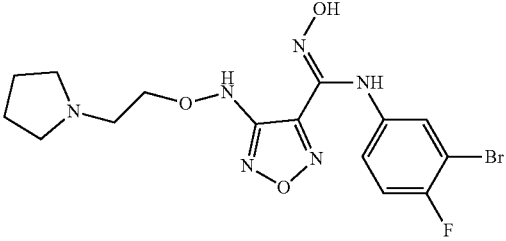<br>I-3 | [M + H]⁺ = 430.6 | 1H NMR (400 MHz, d6-DMSO): 11.09 (s, 1H), 9.15 (s, 1H), 7.18-7.12 (m, 1H), 6.95-6.93 (m, 2H), 6.43 (s, 1H), 1.80-1.78 (m, 2H), 1.65-1.63 (m, 2H), 1.48-1.45 (m, 4H), 1.25-1.23 (m, 4H) ppm. |
| 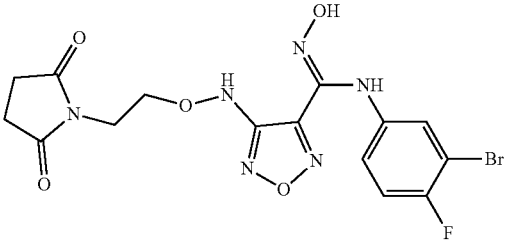<br>I-4 | [M + H]⁺ = 458.3 | 1H NMR (400 MHz, d6-DMSO): 11.21 (s, 1H), 9.80 (s, 1H), 7.66-7.65 (m, 1H), 6.78-6.73 (m, 2H), 6.27 (s, 1H), 3.35-3.30 (m, 2H), 3.13-3.10 (m, 2H), 2.98-2.95 (m, 4H) ppm. |
| 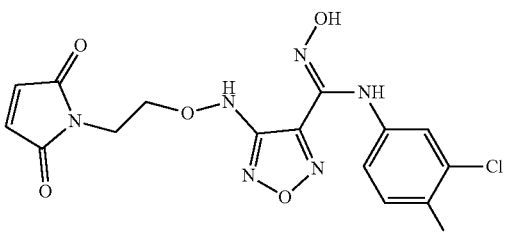<br>I-5 | [M + H]⁺ = 412.5 | 1H NMR (400 MHz, d6-DMSO): 11.35 (s, 1H), 9.92 (s, 1H), 7.65-7.62 (m, 1H), 6.93 (s, 2H), 6.86-6.83 (m, 2H), 6.75 (s, 1H), 3.45-3.43 (m, 2H), 3.18-3.16 (m, 2H) ppm. |
| 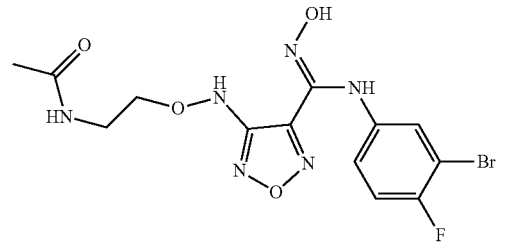<br>I-6 | [M + H]⁺ = 418.2 | 1H NMR (400 MHz, d6-DMSO): 11.26 (s, 1H), 9.82 (s, 1H), 7.65-7.63 (m, 1H), 6.79-6.76 (m, 2H), 6.37 (s, 1H), 4.35 (s, 1H), 3.42-3.38 (m, 2H), 3.10-3.08 (m, 2H), 2.85 (s, 3H) ppm. |
| 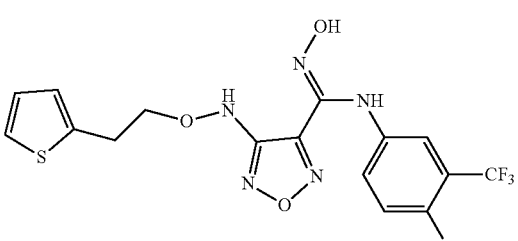<br>I-7 | [M + H]⁺ = 432.1 | 1H NMR (400 MHz, d6-DMSO): 11.20 (s, 1H), 9.15 (s, 1H), 7.50-7.48 (m, 2H), 7.11-7.08 (m, 2H), 6.95-6.93 (m, 2H), 6.80 (s, 1H), 5.05-5.02 (m, 2H), 2.02 (dd, 2H) ppm. |

| Compound structures and numbers | MS | ¹H NMR |
|---|---|---|
| 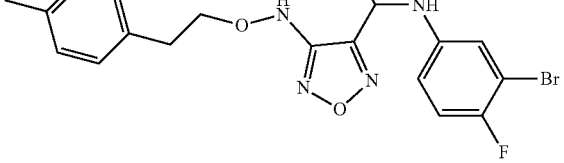<br>I-8 | [M + H]⁺ = 450.1 | 1H NMR (400 MHz, d6-DMSO): 11.12 (s, 1H), 9.32 (s, 1H), 7.60-7.55 (m, 2H), 7.18-7.12 (m, 2H), 6.96-6.94 (m, 2H), 6.76-6.73 (m, 2H), 4.62 (m, 2H), 2.21 (dd, 2H), 1.93 (s, 3H) ppm. |
| 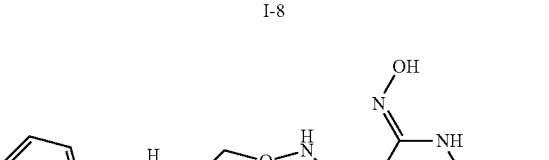<br>I-9 | [M + H]⁺ = 486.9 | 1H NMR (400 MHz, d6-DMSO): 11.35 (s, 1H), 9.95 (s, 1H), 8.23 (s, 1H), 7.75-7.70 (m, 3H), 6.82-6.79 (m, 4H), 6.35 (s, 1H), 3.48-3.42 (m, 2H), 3.15-3.13 (m, 2H) ppm. |
| 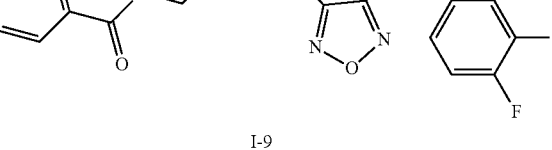<br>I-10 | [M + H]⁺ = 457.8 | 1H NMR (400 MHz, d6-DMSO): 11.53 (s, 1H), 9.86 (s, 1H), 8.36 (s, 1H), 8.16 (s, 1H), 7.85-7.80 (m, 1H), 6.86-6.82 (m, 2H), 6.33 (s, 1H), 5.85 (s, 2H), 3.48-3.42 (m, 2H), 3.15-3.13 (m, 2H) ppm. |
| 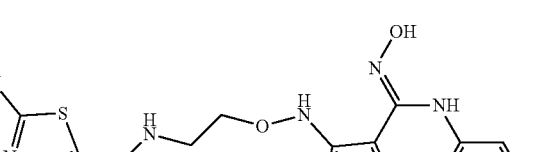<br>I-11 | [M + H]⁺ = 453.3 | 1H NMR (400 MHz, d6-DMSO): 11.17 (s, 1H), 9.32 (s, 1H), 7.50-7.52 (m, 1H), 6.88-6.83 (m, 2H), 6.28 (s, 1H), 2.10-2.08 (m, 2H), 1.98-1.93 (m, 2H) ppm. |
| 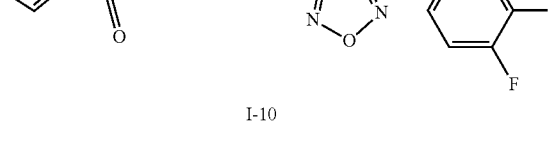<br>I-12 | [M + H]⁺ = 376.3 | 1H NMR (400 MHz, d6-DMSO): 11.30 (s, 1H), 10.02 (s, 1H), 7.68-7.66 (m, 1H), 6.87-6.83 (m, 2H), 6.87 (s, 1H), 3.53 (t, 2H), 3.40-3.36 (m, 2H), 3.14-3.11 (m, 2H) ppm. |

-continued
| Compound structures and numbers | MS | ¹H NMR |
|---|---|---|
| 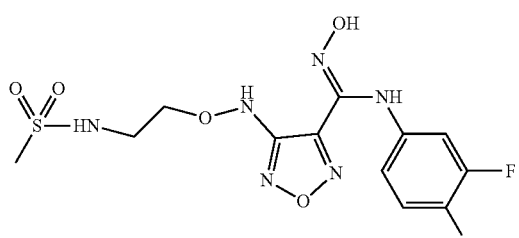 I-13 | [M − H]⁻ = 451.3 | 1H NMR (400 MHz, d6-DMSO): 11.05 (s, 1H), 9.86 (s, 1H), 7.65-7.61 (m, 1H), 6.78-6.74 (m, 2H), 6.48 (s, 1H), 4.32 (s, 1H), 3.48-3.46 (m, 2H), 3.14-3.12 (m, 2H), 2.85 (s, 3H) ppm. |
| 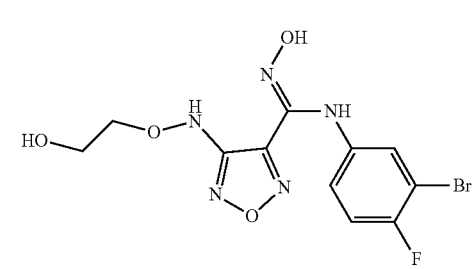 I-14 | [M − H]− 375.2 | 1H-NMR (400 MHz, d6-DMSO): δ = 11.47 (s, 1H), 8.88 (s, 1H), 7.25-7.24 (m, 1H), 7.17-7.09 (m, 1H), 6.88-6.84 (m, 1H), 5.88 (s, 1H), 3.28-3.26 (s, 1H), 1.88-1.84 (m, 2H), 1.65-1.60 (m, 2H) ppm. |
| 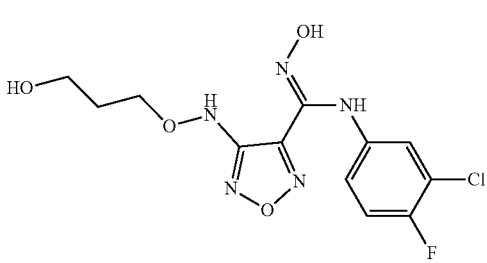 I-15 | [M − H]− 344.6 | 1H-NMR (400 MHz, d6-DMSO): δ = 11.48 (s, 1H), 8.93 (s, 1H), 7.26-7.23 (m, 1H), 7.18-7.12 (m, 1H), 6.88-6.82 (m, 1H), 5.85 (s, 1H), 3.38-3.36 (s, 1H), 1.87-1.86 (m, 2H), 1.64-1.62 (m, 2H), 1.23-1.20 (m, 2H) ppm. |
| 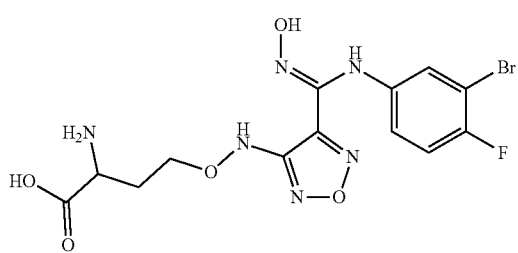 I-16 | [M − H]− 432.3 | 1H-NMR (400 MHz, d6-DMSO): δ = 11.52 (s, 1H), 11.08 (s, 1H), 7.21-7.17 (m, 1H), 7.14-7.11 (m, 1H), 6.36-6.31 (m, 1H), 5.13-5.11 (m, 2H), 4.63-4.59 (m, 2H), 3.59-3.53 (m, 2H), 3.49-3.47 (m, 1H), 1.95-1.92 (m, 2H) ppm |
| 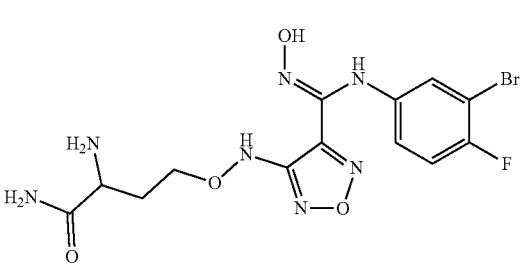 I-17 | [M + H]+ 433.1 | 1H-NMR (400 MHz, d6-DMSO): δ = 11.58 (s, 1H), 8.05 (s, 2H), 7.28-7.26 (m, 1H), 7.17-7.14 (m, 1H), 6.42-6.39 (m, 1H), 5.05-5.02 (m, 2H), 4.68-4.65 (m, 2H), 3.63-3.58 (m, 2H), 3.50-3.47 (m, 1H), 1.88-1.82 (m, 2H) ppm |

-continued
| Compound structures and numbers | MS | ¹H NMR |
|---|---|---|
| 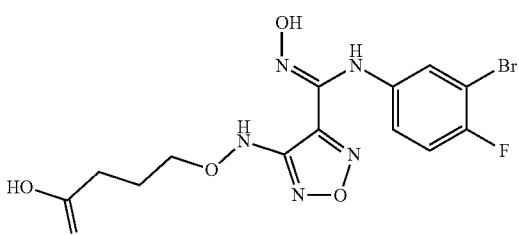 I-18 | [M − H]− 417.2 | 1H-NMR (400 MHz, d6-DMSO): δ = 11.43 (s, 1H), 11.25 (s, 1H), 7.35-7.31 (m, 1H), 7.27-7.25 (m, 1H), 6.32-6.29 (m, 1H), 4.05-4.02 (m, 2H), 3.53-3.51 (m, 2H), 2.30-2.26 (, 2H), 1.83-1.81 (m, 2H) ppm |
| 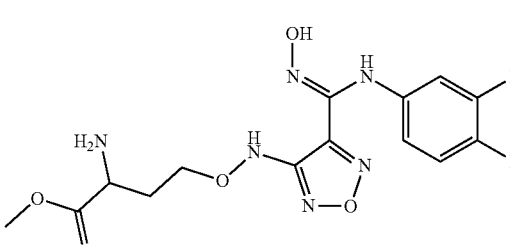 I-19 | [M + H]+ 448.3 | 1H-NMR (400 MHz, d6-DMSO): δ = 11.48 (s, 1H), 7.25-7.21 (m, 1H), 7.18-7.15 (m, 1H), 6.38-6.36 (m, 1H), 5.23-5.19 (m, 2H), 4.66-4.60 (m, 2H), 3.70 (s, 3H), 3.63-3.60 (m, 2H), 3.44-3.41 (m, 1H), 1.85-1.83 (m, 2H) ppm |
| 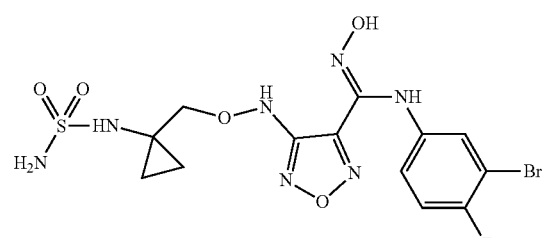 I-20 | [M − H]− 480.1 | 1H-NMR (400 MHz, d6-DMSO): δ = 11.51 (s, 1H), 9.62 (s, 1H), 8.95 (s, 1H), 7.19-7.07 (m, 3H), 6.76-6.64 (m, 3H), 3.95 (s, 2H), 1.24-1.23 (m, 2H), 0.96-0.89 (m, 2H) ppm. |
| 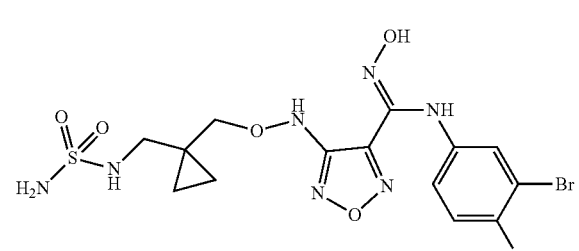 I-21 | [M + H]+ 495.3 | 1H-NMR (400 MHz, d₆-DMSO): 11.53 (s, 1H), 8.96 (s, 1H), 7.20-7.18 (m, 1H), 7.15-7.13 (m, 1H), 6.78-6.75 (m, 1H), 6.70 (t, 1H), 6.45 (s, 2H), 6.16 (t, 1H), 3.25 (d, 2H), 2.83 (d, 2H), 1.03 (s, 4H) ppm. |
| 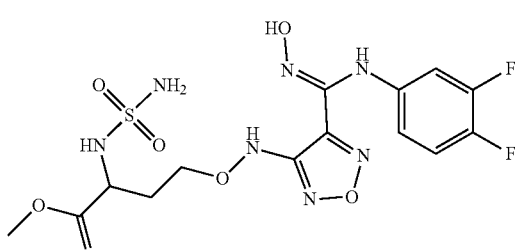 I-22 | [M − H]+ 466.4 | 1H-NMR (400 MHz, d₆-DMSO): δ = 11.56 (s, 1H), 9.67 (s, 1H), 8.86 (s, 1H), 7.28-7.26 (m, 1H), 7.15-7.12 (m, 1H), 6.99-6.95 (m, 1H), 6.62-6.60 (m, 2H), 6.58-6.55 (m, 1H), 3.96-3.93 (m, 2H), 3.73 (s, 3H), 3.65-3.60 (m, 1H), 3.11-3.08 (m, 2H) ppm |

-continued
| Compound structures and numbers | MS | ¹H NMR |
|---|---|---|
| 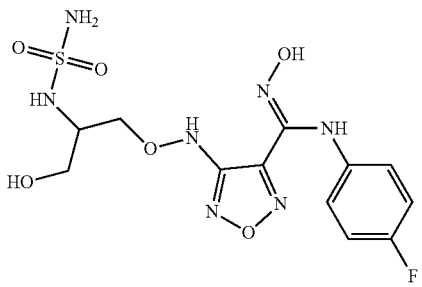<br>I-23 | [M + H]⁺ 406.1 | 1H-NMR (400 MHz, d6-DMSO): δ = 11.32 (s, 1H), 8.95 (s, 1H), 7.19-7.15 (m, 2H), 6.84-6.82 (m, 1H), 6.66-6.65 (m, 1H), 6.45-6.40 (m, 1H), 6.31 (m, 1H), 6.26-6.23 (m, 1H), 4.62 (t, 1H), 4.01-3.98 (m, 1H), 3.44-3.41 (m, 3H), 3.13-3.08 (m, 1H) ppm |
| 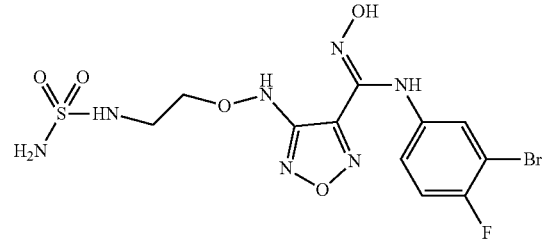<br>I-24 | [M − H]− 453.7 | 1H-NMR (400 MHz, d6-DMSO): δ = 11.54 (s, 1H), 9.68 (s, 1H), 8.95 (s, 1H), 7.22-7.18 (t, 1H), 7.12-7.10 (m, 1H), 6.79-6.75 (m, 1H), 6.62 (s, 2H), 6.56-6.53 (t, 1H), 3.96-3.93 (m, 2H), 3.17-3.15 (m, 2H) ppm. |
| 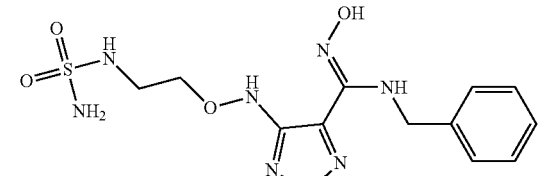<br>I-25 | [M − H]− 370.2 | 1H-NMR (400 MHz, d6-DMSO): δ = 11.51 (s, 1H), 9.64 (s, 1H), 8.93 (s, 1H), 7.26-7.19 (m, 2H), 7.15-7.06 (m, 3H), 6.82-6.78 (m, 1H), 6.54-6.50 (m, 2H), 3.86-3.83 (m, 2H), 3.62-3.59 (m, 2H), 3.22-3.18 (m, 2H) ppm |
| 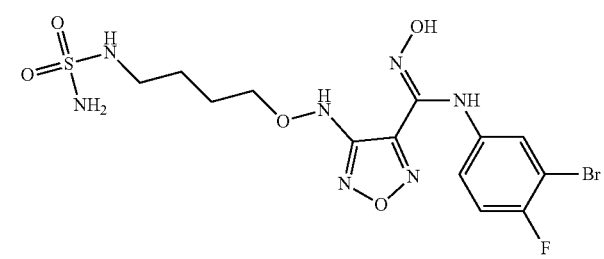<br>I-26 | [M − H]− 481.6 | 1H-NMR (400 MHz, d6-DMSO): δ = 11.55 (s, 1H), 9.66 (s, 1H), 8.89 (s, 1H), 7.27-7.25 (m, 1H), 7.16-7.13 (m, 1H), 6.88-6.83 (m, 1H), 6.65 (s, 2H), 6.59-6.57 (m, 1H), 3.92-3.89 (m, 2H), 3.87-3.85 (m, 2H), 3.33-3.28 (m, 2H), 3.20-3.14 (m, 2H) ppm |
| 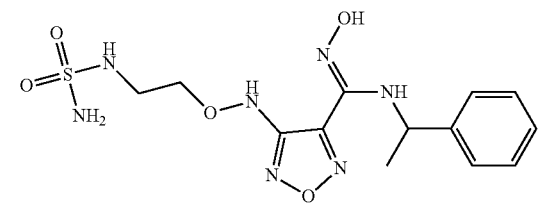<br>I-27 | [M − H]− 384.4 | 1H-NMR (400 MHz, d6-DMSO): δ = 11.50 (s, 1H), 9.67 (s, 1H), 8.98 (s, 2H), 7.26-7.22 (m, 2H), 7.19-7.08 (m, 3H), 6.86-6.84 (m, 1H), 6.55-6.51 (m, 2H), 3.90-3.87 (m, 2H), 3.58-3.53 (m, 1H), 3.25-3.20 (m, 2H), 1.28-1.22 (m, 3H) ppm. |

-continued
| Compound structures and numbers | MS | ¹H NMR |
|---|---|---|
| 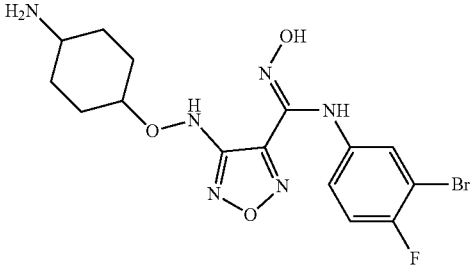<br>I-28 | [M + H]⁺ 430.6 | 1H-NMR (400 MHz, d6-DMSO): δ = 11.51 (s, 1H), 9.64 (s, 1H), 8.93 (s, 1H), 7.19-7.16 (m, 1H), 6.94-6.92 (m, 1H), 6.01 (m, 1H), 3.26-3.23 (m, 2H), 3.05-3.02 (d, 2H), 2.13-2.08 (m, 4H), 1.56-1.52 (m, 4H) ppm. |
| 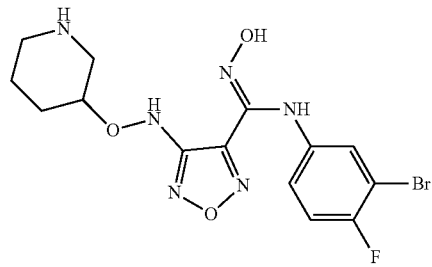<br>I-29 | [M + H]⁺ 416.3 | 1H-NMR (400 MHz, d6-DMSO): δ = 11.45 (s, 1H), 8.90 (s, 1H), 7.22-7.18 (t, 1H), 7.12-7.09 (m, 1H), 6.78-6.75 (m, 1H), 6.18-6.15 (m, 1H), 3.90-3.89 (m, 2H), 3.57-3.55 (m, 1H), 3.33-3.28 (m, 2H), 2.20-2.14 (m, 1H), 1.93-1.92 (m, 2H), 1.45-1.43 (m, 6H) ppm. |
| 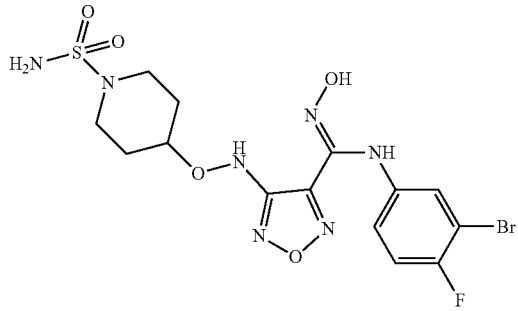<br>I-30 | [M + H]+ 495.0 | 1H-NMR (400 MHz, d6-DMSO): δ = 11.50 (s, 1H), 8.93 (s, 1H), 7.18-7.16 (m, 1H), 6.90-6.79 (m, 1H), 6.37-6.35 (m, 1H), 6.13 (s, 1H), 3.42-3.40 (m, 1H), 3.21 (s, 2H), 3.08-3.05 (m, 1H), 2.11-2.08 (m, 4H), 1.86-1.82 (m, 4H) ppm. |
| 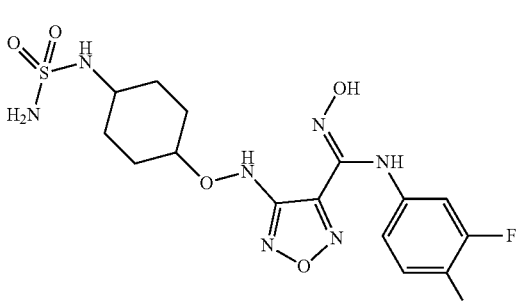<br>I-31 | [M + H]+ 448.2 | 1H-NMR (400 MHz, d6-DMSO): δ = 11.51 (s, 1H), 9.64 (s, 1H), 8.93 (s, 1H), 7.19-7.16 (m, 1H), 6.94-6.92 (m, 1H), 6.67-6.65 (m, 3H), 6.01 (m, 1H), 3.26-3.23 (m, 1H), 3.05-3.02 (m, 1H), 2.13-2.08 (m, 4H), 1.56-1.52 (m, 4H) ppm. |
| 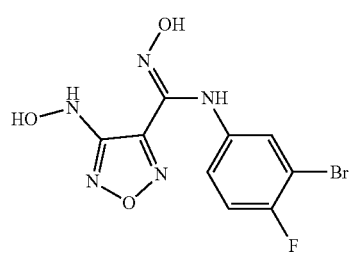<br>I-32 | [M + H]+ = 333.5 | 1H NMR (400 MHz, d6-DMSO): 11.30 (s, 1H), 8.92 (s, 1H), 7.18-7.15 (m, 2H), 7.06-7.05 (d, 1H), 6.90-6.88 (m, 1H), 4.50 (d, 1H) ppm. |

-continued
| Compound structures and numbers | MS | ¹H NMR |
|---|---|---|
| 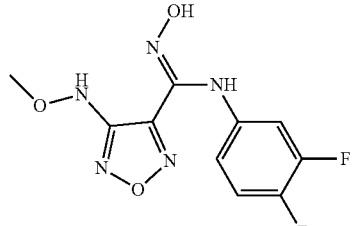 I-33 | [M + H]+ = 272.2 | 1H NMR (400 MHz, d6-DMSO): 11.42 (s, 1H), 8.98 (s, 1H), 7.16-7.14 (m, 2H), 7.05-7.02 (d, 1H), 6.90-6.86 (m, 1H), 4.55 (d, 1H) ppm. |
| 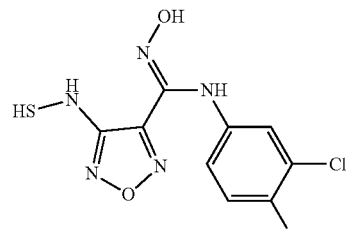 I-34 | [M + H]+ = 304.8 | 1H NMR (400 MHz, d6-DMSO): 11.22 (s, 1H), 8.96 (s, 1H), 7.15-7.13 (m, 2H), 7.08-7.06 (d, 1H), 6.91-6.88 (m, 1H), 3.58 (d, 1H) ppm. |
| 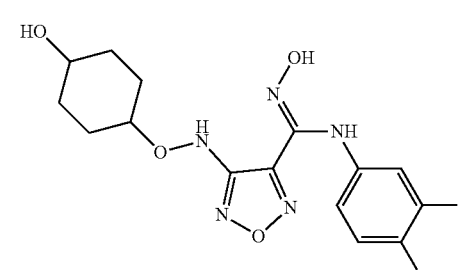 I-35 | [M − H]− 370.2 | 1H-NMR (400 MHz, d6-DMSO): δ = 11.52 (s, 1H), 8.93 (s, 1H), 7.26-7.22 (m, 1H), 7.19-7.08 (m, 1H), 6.86-6.84 (m, 1H), 5.89-5.85 (m, 2H), 4.59-4.56 (m, 1H), 3.46-3.45 (m, 1H), 3.28-3.26 (m, 1H), 1.85-1.83 (m, 2H), 1.25-1.20 (m, 4H) ppm. |
| 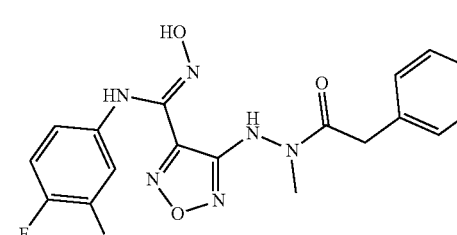 I-36 | [M + H]+ 462.9 | 1H-NMR (400 MHz, d6-DMSO): δ = 11.08 (s, 1H), 10.37 (s, 1H), 8.99 (s, 1H), 7.27-7.11 (m, 8H), 6.72-6.70 (m, 1H), 3.40 (s, 2H), 3.07 (s, 3H) ppm. |
| 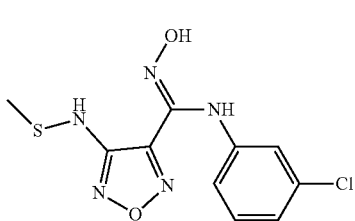 I-37 | [M + H]+ = 318.7 | 1H NMR (400 MHz, d6-DMSO): 11.62 (s, 1H), 9.21 (s, 1H), 7.55-7.53 (m, 2H), 7.18-7.16 (d, 1H), 6.81-6.80 (m, 1H), 2.12 (s, 3H) ppm. |

-continued
| Compound structures and numbers | MS | ¹H NMR |
|---|---|---|
| 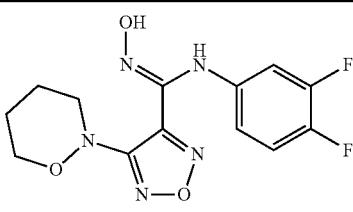 I-38 | [M + H]+ = 326.1 | 1H NMR (400 MHz, d6-DMSO): 11.03 (s, 1H), 9.12 (s, 1H), 7.18-7.12 (m, 1H), 6.76-6.73 (m, 2H), 2.23-2.21 (m, 4H), 1.90-1.88 (m, 4H) ppm. |
| 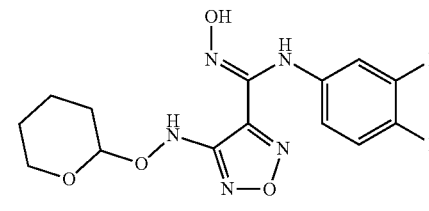 I-39 | [M + H]+ = 356.0 | 1H NMR (400 MHz, d6-DMSO): 11.16 (s, 1H), 9.11 (s, 1H), 7.16-7.12 (m, 1H), 6.98-6.96 (m, 2H), 6.73 (s, 1H), 2.25-2.23 (t, 1H), 1.90-1.88 (m, 4H), 1.20-1.16 (m, 4H) ppm. |
| 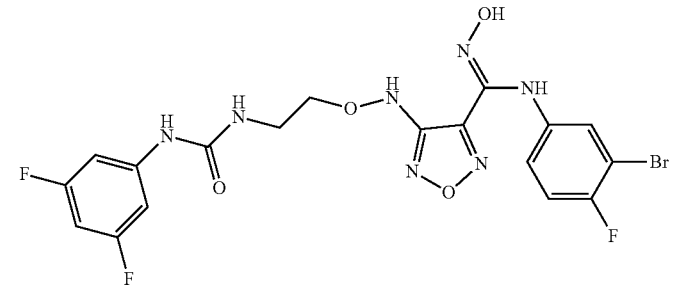 I-40 | [M + H]+ = 531.3 | 1H NMR (400 MHz, d6-DMSO): 11.35 (s, 1H), 9.76 (s, 1H), 8.56 (s, 1H), 8.26-8.23 (m, 1H), 7.82-7.81 (m, 2H), 6.96-6.94 (m, 4H), 6.43 (s, 1H), 3.47-3.42 (m, 2H), 3.16-3.13 (m, 2H) ppm. |
| 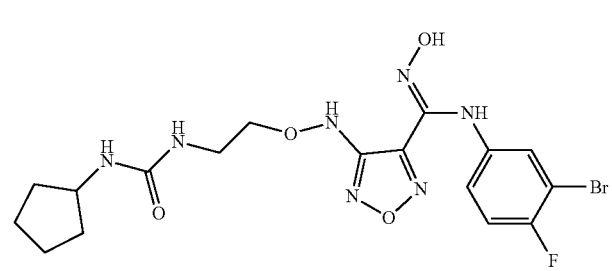 I-41 | [M + H]+ = 487.3 | 1H NMR (400 MHz, d6-DMSO): 11.13 (s, 1H), 9.66 (s, 1H), 7.64-7.60 (m, 1H), 6.76-6.74 (m, 2H), 6.43 (s, 1H), 4.30-4.28 (m, 2H), 3.49-3.45 (m, 2H), 3.15-3.13 (m, 2H), 2.82-2.80 (m, 1H), 1.78-1.75 (m, 4H), 1.34-1.30 (m, 4H) ppm. |
| 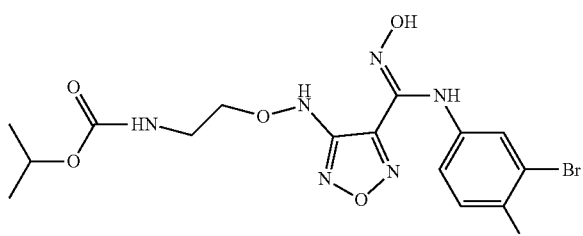 I-42 | [M + H]+ = 462.5 | 1H NMR (400 MHz, d6-DMSO): 11.09 (s, 1H), 9.76 (s, 1H), 7.65-7.63 (m, 1H), 6.82-6.80 (m, 2H), 6.45 (s, 1H), 4.33-4.29 (m, 2H), 3.48-3.46 (m, 2H), 3.23-3.20 (m, 1H), 2.77-2.75 (m, 1H), 1.43-1.41 (m, 6H) ppm. |

-continued

| Compound structures and numbers | MS | ¹H NMR |
|---|---|---|
| I-43 | [M − H]− 689.2 | 1H-NMR (400 MHz, d6-DMSO): δ = 11.49 (s, 2H), 8.90 (s, 2H), 7.29-7.11 (m, 4H), 6.77-6.73 (m, 2H), 6.36-6.32 (m, 2H), 3.47-3.46 (m, 4H) ppm. |
| I-44 | [M − H]− 485.5 | 1H-NMR (400 MHz, d6-DMSO): δ = 11.56 (s, 1H), 9.69 (s, 1H), 8.85 (s, 1H), 7.20-7.18 (t, 1H), 7.12-7.10 (m, 1H), 6.79-6.76 (m, 1H), 6.68 (s, 2H), 6.55-6.54 (t, 1H), 3.96-3.95 (m, 2H), 3.16-3.15 (m, 2H) ppm. |
| I-45 | [M + H]+ = 374.9 | 1H NMR (400 MHz, d6-DMSO): 11.05 (s, 1H), 9.65 (s, 1H), 7.53-7.50 (m, 1H), 6.86-6.83 (m, 2H), 6.18 (s, 1H), 2.18 (s, 3H) ppm. |
| I-46 | [M + H]+ = 437.0 | 1H NMR (400 MHz, d6-DMSO): 11.26 (s, 1H), 9.78 (s, 1H), 7.50-7.45 (m, 4H), 6.85-6.82 (m, 4H), 6.78 (s, 1H) ppm. |
| I-47 | [M + H]+ = 452.0 | 1H NMR (400 MHz, d6-DMSO): 11.06 (s, 1H), 9.98 (s, 1H), 7.51-7.48 (m, 4H), 7.12-7.08 (s, 1H), 6.65-6.62 (m, 4H), 6.78 (s, 1H) ppm. |

-continued
| Compound structures and numbers | MS | ¹H NMR |
|---|---|---|
| 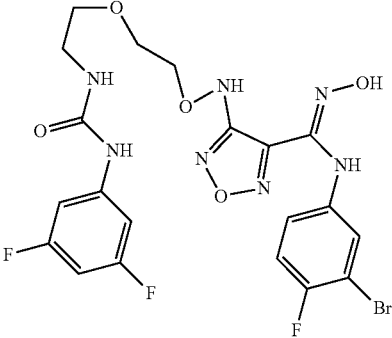<br>I-48 | [M + H]+ 575.6 | 1H-NMR (400 MHz, d6-DMSO): δ = 11.47 (s, 1H), 8.93 (s, 1H), 7.19-7.16 (m, 3H), 6.94-6.92 (m, 1H), 6.67-6.65 (m, 3H), 6.01 (m, 1H), 3.26-3.23 (m, 1H), 2.32-2.30 (m, 2H), 2.13-2.08 (m, 4H), 1.86-1.82 (m, 2H) ppm. |
| 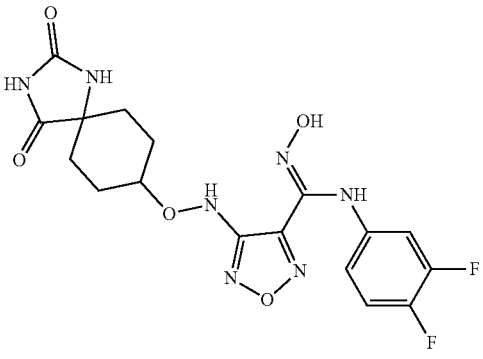<br>I-49 | [M + H]+ 438.4 | 1H-NMR (400 MHz, d6-DMSO): δ = 11.53 (s, 1H), 8.82 (s, 1H), 7.21-7.19 (m, 1H), 6.93-6.89 (m, 1H), 6.47-6.45 (m, 1H), 6.23 (s, 1H), 3.62-3.61 (s, 2H), 3.45-3.43 (m, 1H), 1.96-1.93 (m, 4H), 1.84-1.82 (m, 4H) ppm. |
| 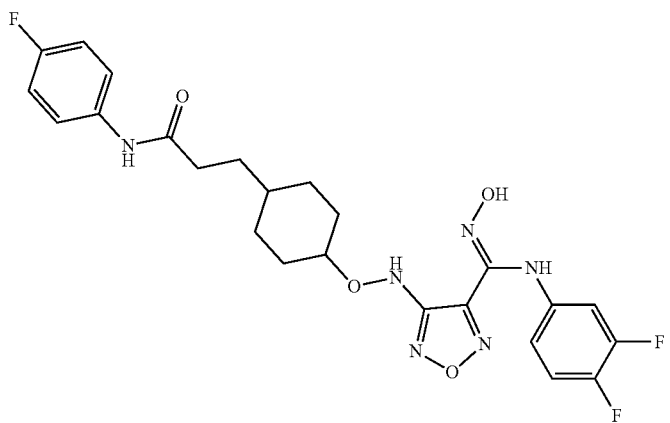<br>I-50 | [M + H]+ 519.5 | 1H-NMR (400 MHz, d6-DMSO): δ = 11.43 (s, 1H), 9.44 (s, 1H), 8.93 (s, 1H), 7.19-7.16 (m, 1H), 6.94-6.92 (m, 3H), 6.65-6.61 (m, 3H), 6.12 (s, 1H), 3.26-3.23 (m, 2H), 3.15-3.12 (m, 2H), 1.85-1.83 (m, 1H), 1.54-1.50 (m, 8H) ppm. |
| 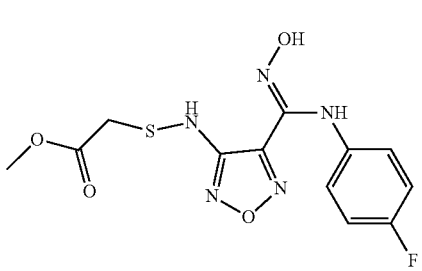<br>I-51 | [M + H]⁺ = 342.6 | 1H NMR (400 MHz, d6-DMSO): 10.87 (s, 1H), 9.31 (s, 1H), 7.54-7.51 (m, 1H), 6.88-6.85 (m, 2H), 6.38 (s, 1H), 3.43 (s, 3H), 3.10 (s, 2H) ppm. |

Biological Evaluation

Test Example 1. Determination of the IDO1 Inhibitory Activity of Compounds

The present disclosure is further explained below in combination with test examples, but these test examples are not meant to limit the present disclosure. The following disclosures show the inhibitory activity of some compounds of the invention on IDO1 enzyme. The structure formula of the compounds is shown in the examples above.

1. Materials, Kits and Equipments

Sodium L-ascorbate (Cat: A4034-100G, SIGMA)

4-(dimethylamino)benzaldehyde (Cat: 156477-25g, SIGMA)

Trichloroacetic acid (Cat: T0699-100ML, SIGMA)

L-Tryptophan (Cat: T8941-25G, SIGMA)

Methylene blue (Cat: M9140-25G, SIGMA)

Potassium dihydrogen phosphate (Cat: 10017618, Sinopharm Chemical Reagent)

Disodium hydrogen phosphate (Cat: 20040618, Sinopharm Chemical Reagent)

Constant temperature water tank (Cat: DK-8D, Shanghai Jinghong Experimental Equipment)

Multifunctional microplate reader (Cat: M5, Molecular Devices)

96-well reaction plate (Cat: 3590, costar)

IDO1 protease (commercially available)

Desktop Microplate Reader: SpectraMax M5 Microplate Reader (Molecular Devices)

Test compounds: self-made

Positive control agent: INCB024360 (commercially available)

2. Reagent Preparation 100 mM PBS:

100 mM disodium hydrogen phosphate and 100 mM potassium dihydrogen phosphate mixed in a ratio of 3:5, pH 6.5

IDO1 assay buffer:

100 mM PBS containing 400 µM L-tryptophan, 20 mM ascorbate, 20 µM methylene blue and 1000 U/ml catalase, pH 6.5

30% trichloroacetic acid ddH$_2$O solution of 30% trichloroacetic acid

Ehrlich reagent

1% (w/v) diluted solution of 4-(dimethylamino) benzaldehyde compound

All compounds were dissolved with DMSO. During the assay, each compound was diluted to a concentration as needed. The compound of each concentration was added to multi-wells, and the final concentration of DMSO was controlled at 1%.

3. Test Method a.) the reaction mixture was prepared by adding 50 nM IDO1 and the desired concentration of the test compound to 100 µL of IDO1 assay buffer. IDO1 and assay buffer need to be preheated to 37° C.

b.) The mixture was reacted in a constant temperature water tank at 37° C. for 30 minutes.

c.) 50 µL of 30% trichloroacetic acid was added.

d.) The above mixture was reacted in a constant temperature water tank at 52° C. for 30 minutes.

e.) The reaction mixture was centrifuged at 12000 g for 10 minutes at room temperature.

f.) 100 µL of the obtained supernatant and 100 µL of Ehrlich reagent were mixed.

g.) the absorbance at 480 nm was measured using an M5 microplate reader.

4. Data Analysis

Inhibition rate=(OD$_{postive}$−OD$_{sample}$)/(OD$_{postive}$−OD$_{negative}$)*100%

5. Results and Discussion

In this experiment, the inhibitory activity of the test compounds on the IDO1 enzyme was tested. Compounds of each diluted concentration were tested in multi-wells. The final concentration of the reaction system in DMSO was controlled to 1%. The inhibition rate was tested twice, and the average value was taken. The experimental results are in the table below, which show that the compounds of the present disclosure exhibit good inhibitory activity against IDO1 protease.

Inhibitory Activity of Test Compounds on IDO1 Enzyme

| Compound No. | IC$_{50}$(nm) |
|---|---|
| I-1 | 80 |
| I-2 | 43 |
| I-3 | 108 |
| I-4 | 96 |
| I-5 | 32 |
| I-6 | 162 |
| I-7 | 113 |
| I-8 | 94 |
| I-9 | 85 |
| I-10 | 90 |
| I-11 | 120 |
| I-12 | 35 |
| I-13 | 124 |
| I-14 | 81 |
| I-15 | 93 |
| I-16 | 42 |
| I-17 | 85 |
| I-18 | 183 |
| I-19 | 140 |
| I-20 | 18 |
| I-21 | 82 |
| I-22 | 64 |
| I-23 | 36 |
| I-24 | 8 |
| I-25 | 68 |
| I-26 | 92 |
| I-27 | 42 |
| I-28 | 184 |
| I-29 | 80 |
| I-30 | 65 |
| I-31 | 42 |
| I-32 | 125 |
| I-33 | 99 |
| I-34 | 104 |
| I-35 | 94 |
| I-36 | 82 |
| I-37 | 53 |
| I-38 | 78 |
| I-39 | 142 |
| I-40 | 12 |
| I-41 | 69 |
| I-42 | 36 |
| I-43 | 35 |
| I-44 | 78 |
| I-45 | 92 |
| I-46 | 65 |
| I-47 | 48 |
| I-48 | 72 |
| I-49 | 66 |
| I-50 | 28 |
| I-51 | 83 |
| INCB024360 | 32 |

Conclusion: the assay results show that the compound of the invention has a significant inhibitory effect on IDO, and the effect is comparable or even better than INCB024360.

Test Example 2. Determination of the Inhibitory Activity of Compounds on IDO Protease in Highly Expressed HeLa Cells This method was used to determine the inhibitory effect of the compounds of the invention on the inhibitory activity of IDO protease in highly expressed HeLa cells.
1. Reagents and Materials:
Desktop Microplate Reader SpectraMax M5 Microplate Reader (Molecular Devices)
Multifunctional microplate reader (Cat: M5, Molecular Devices)
L-Tryptophan (Cat: T8941-25G, SIGMA)
4-(dimethylamino)benzaldehyde (Cat: 156477-25g, SIGMA)
Trichloroacetic acid (Cat: T0699-100ML, SIGMA)
Highly expressed HeLa cell line
2. Test Method
a.) 50 µL of 30% trichloroacetic acid was added.
b.) The mixture was reacted in a constant temperature water tank at 52° C. for 30 minutes.
c.) The above mixture was centrifuge at 12,000 g for 10 minutes at room temperature.
d.) 100 µL of the supernatant was mixed with 100 µL of Ehrlich reagent.
e.) the absorbance was measured at 480 nm using an M5 microplate reader.
3. Data Processing
The inhibition rate of the tumor cell growth was calculated by the following formula: tumor cell growth inhibition rate %=[(Ac−As)/(Ac−Ab)]×100%
The software Graphpad Prism 5 was used with the calculation formula of log(inhibitor) vs. normalized response to perform $IC_{50}$ curve fitting and the $IC_{50}$ value was calculated. The results are shown in the following table:

| Compound No. | $IC_{50}$(nm) |
|---|---|
| I-2 | 38 |
| I-5 | 58 |
| I-12 | 43 |
| I-16 | 35 |
| I-20 | 8 |
| I-23 | 38 |
| I-24 | 5 |
| I-27 | 26 |
| I-40 | 12 |
| I-42 | 28 |
| I-43 | 38 |
| I-47 | 47 |
| I-50 | 21 |
| INCB024360 | 33 |

Conclusion: the test results show that the compound of the invention has a significant inhibitory effect on HeLa intracellular IDO protease.

Test Example 3. Pharmacokinetic Evaluation

Pharmacokinetic tests were conducted on compounds I-20, I-24, I-40 of the invention and the compound INCB024360 to study their pharmacokinetic behavior in rats and evaluate their pharmacokinetic characteristics.
1. Experimental animals: 100 (half male and half female) SPF grade SD rats were purchased from Shanghai Cypre- Bikai Experimental Animal Co., Ltd. Among them, 72 medically qualified and healthy SD rats without abnormality (half male and half female) were used for the study.
2. Animal Administration
72 SD rats (half male and half female) were tested according to the following table. The drug samples were stirred at least 10 minutes before administration.

| Group No. | Test substance | Dosage[a] mg/kg | Administration concentration mg/mL | Administration volume mL/kg | Mode of administration |
|---|---|---|---|---|---|
| 1 | I-20 | 75 | 7.5 | 10 | PO[b] |
| 2 | I-24 | 75 | 7.5 | 10 | PO[b] |
| 3 | I-40 | 75 | 7.5 | 10 | PO[b] |
| 4 | INCB024360 | 75 | 7.5 | 10 | PO[b] |

Note:
*Before oral administration, all animals were fasted overnight (10-14 hours) and fed 4 hours after administration.

3. Sample Collection and Processing
Blood samples were obtained through the jugular vein puncture, and each sample was collected for about 0.25 mL and added with heparin sodium for anticoagulation. The blood sampling was performed at time points as follows: for oral administration group, before administration, 0.25 h, 0.5 h, 1 h, 2 h, 4 h, 6 h, 8 h, 24 h after administration.

After collection, the blood samples were placed on ice and the plasma was separated by centrifugation (centrifugation conditions: 8000 rpm, 6 minutes, 2-8° C.). The collected plasma was stored at −80° C. before analysis. Plasma samples were analyzed by the analysis department of the experimental institution using LC-MS/MS for the content of the test compound in the rat plasma. The LLOQ of the detection substance was 1 ng/mL.
4. Pharmacokinetic Analysis
According to the blood plasma concentration data of the drugs, the pharmacokinetic calculation software WinNonlin5.2 non-compartmental model was used to calculate the pharmacokinetic parameters $AUC_{0-t}$, Cmax, Tmax, $T_{1/2\ d}$ and other parameters of the test samples and their average value and standard deviation.

When pharmacokinetic parameters were calculated for samples with lower concentration than the lower limit of quantification, samples taken before the curve reached Cmax should be calculated with zero value, and samples taken after the curve reached Cmax should be calculated with non-quantitative (BLQ).
5. Results and Discussion
Main Pharmacokinetic Parameters
According to the blood plasma concentration data of the drugs, the pharmacokinetic parameters of I-20, I-24, I-40, INCB024360 were respectively calculated using the pharmacokinetic calculation software WinNonlin5.2 non-compartment model, and provided in the table below.

The main pharmacokinetic parameters of compounds in SD rats plasma after oral administration by single gavage

| Group No. | Gender F/M | $t_{1/2}$ h | $T_{max}$ h | $C_{max}$ ng/mL | $AUC_{(0-\infty)}$ ng/mL*h |
|---|---|---|---|---|---|
| I-24 | M | 2.12 | 1.0 | 8761.8 | 20653.4 |
|  | F | 2.34 | 1.0 | 7243.3 | 18743.9 |
| I-20 | M | 1.98 | 1.0 | 4238.3 | 2385.3 |
|  | F | 1.42 | 0.5 | 3325.8 | 1985.5 |
| I-40 | M | 1.67 | 1.0 | 4761.8 | 8253.4 |
|  | F | 1.45 | 1.0 | 4243.3 | 7543.9 |

| Group No. | Gender F/M | $t^{1/2}$ h | $T_{max}$ h | $C_{max}$ ng/mL | $AUC_{(0-\infty)}$ ng/mL*h |
|---|---|---|---|---|---|
| INCB024360 | M | 2.24 | 0.5 | 3937.4 | 12164.3 |
| | F | 2.51 | 1.0 | 3412.8 | 11296.9 |

Conclusion: The compound of the invention has good pharmacokinetic absorption and obvious pharmacokinetic absorption effect. Compared with INCB024360, the compound of the invention has better pharmacokinetic properties and broad market prospects.

What we claimed is:

1. A compound having the structure as shown in formula I or formula II, and a salt or stereoisomer thereof:

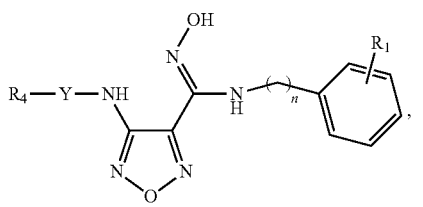

I

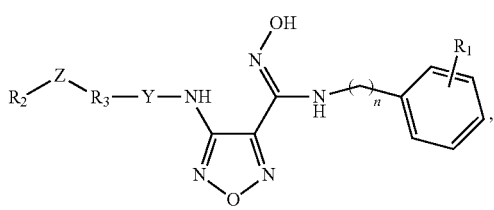

II wherein, in formula I and formula II, $R_1$ is independently selected from hydrogen atom, halogen, and trifluoromethyl;

n represents 0 or 1;

Y is independently selected from oxygen atom, sulfur atom, nitrogen atom, and

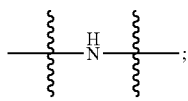

Z is independently selected from oxygen atom, sulfur atom, nitrogen atom, and

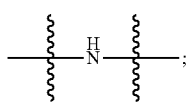

$R_3$ is independently selected from substituted $C_{1-10}$ alkyl and $C_{3-10}$ cycloalkyl, and unsubstituted $C_{1-10}$ alkyl and $C_{3-10}$ cycloalkyl, and the substituent is selected from one or more of amino, oxy, $C_{3-6}$ cycloalkyl, $C_{2-6}$ ester group, $C_{1-6}$ alkyl hydroxyl group, —$CONH_2$;

$R_4$ is independently selected from one of hydrogen atom,

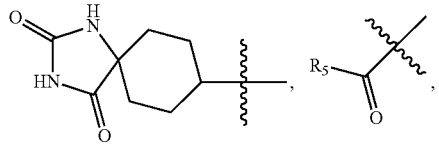

substituted $C_{1-10}$ alkyl, and unsubstituted $C_{1-10}$ alkyl; wherein the substituent of $C_{1-10}$ alkyl is independently selected from one or more of

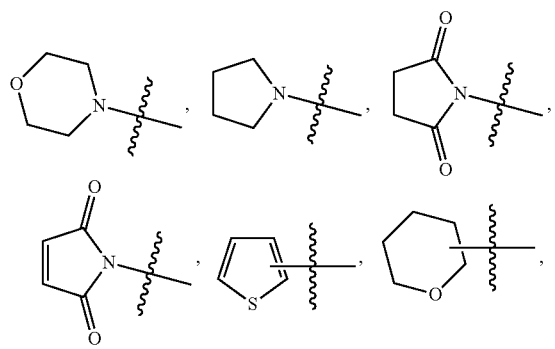

unsubstituted phenyl, and phenyl substituted with $C_{1-4}$ alkyl;

$R_2$ is independently selected from hydrogen atom, $C_{1-6}$ alkyl, $C_{2-6}$ ester group,

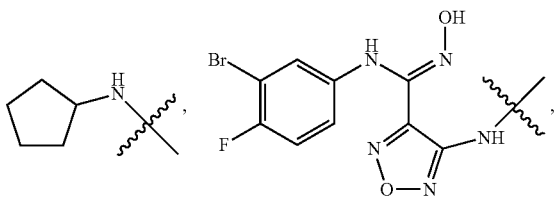 [SMILES: *NC1CCCC1 ; *Nc1nonc1/C(=N/O)Nc1ccc(F)c(Br)c1]

sulfonyl substituted with $C_{1-4}$ alkyl, sulfonyl substituted with amino, sulfonamido substituted with amino,

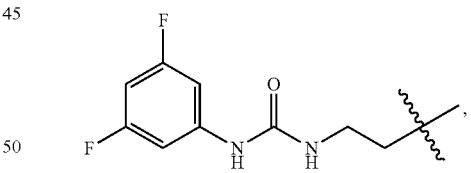

substituted and unsubstituted $C_{4-8}$ aryl, substituted and unsubstituted heteroaryl,

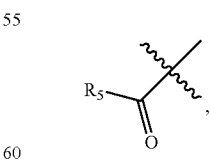

said $R_5$ is independently selected from $C_{1-6}$ alkyl, $C_{1-6}$ alkoxy, substituted and unsubstituted anilino, substituted and unsubstituted $C_{5-12}$ aryl, and substituted and unsubstituted $C_{4-10}$ heteroaryl, and wherein each of the substituted anilino, the substituted $C_{5-12}$ aryl, and the substituted $C_{4-10}$ is independently substituted by halogen, amino, or both.

2. The compound, the salt or stereoisomer thereof according to claim 1, wherein Z and $R_3$ together form a 5-8 membered heterocycloalkyl.

3. The compound, the salt or stereoisomer thereof according to claim 1, wherein Y, Z, and $R_3$ together form a 5-8 membered heterocycloalkyl.

4. The compound, the salt or stereoisomer thereof according to claim 1, wherein $R_2$ is

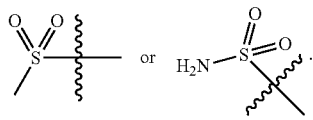

5. The compound, the salt or stereoisomer thereof according to claim 1, wherein n is 1, the group $R_2$ is

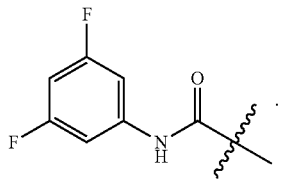 [SMILES: *C(=O)Nc1cc(F)cc(F)c1]

6. The compound, the salt or stereoisomer thereof according to claim 1, wherein $R_4$ is selected from a plurality of $C_{1-10}$ alkyls, each terminated

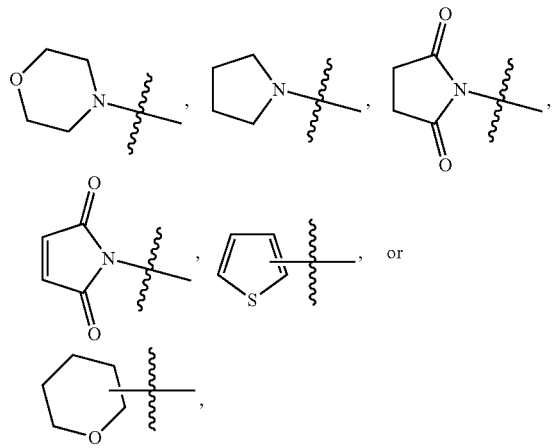

unsubstituted phenyl, and phenyl substituted with $C_{1-4}$ alkyl.

7. A compound, a salt or stereoisomer thereof, wherein the compound is selected from

I-1

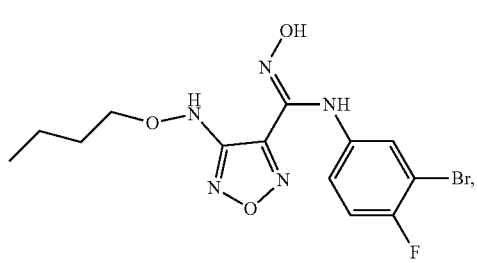

I-2

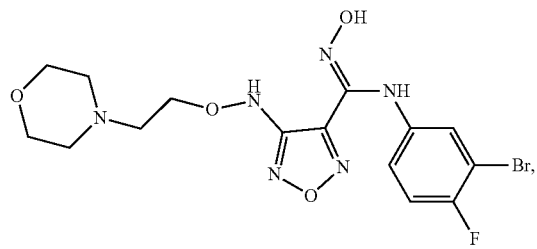

I-3

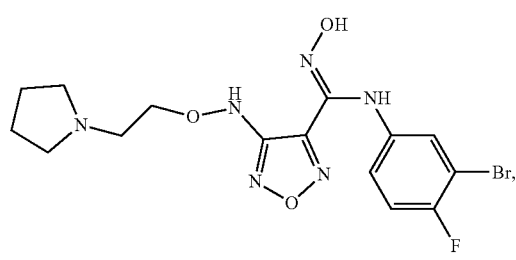

I-4

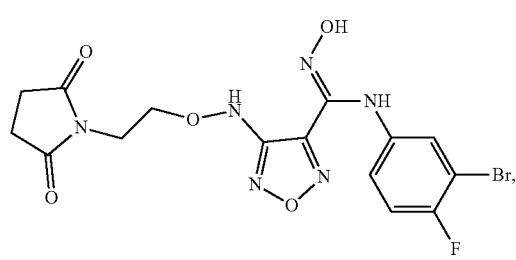

I-5

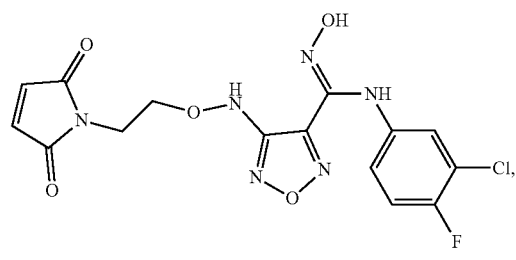

I-6

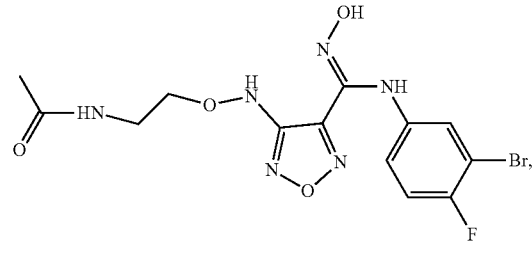

I-7

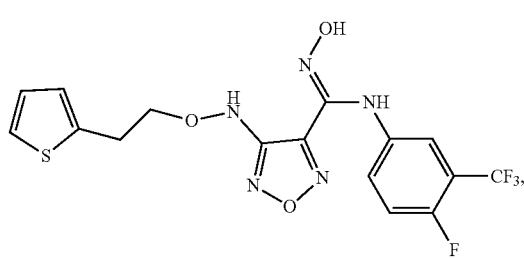

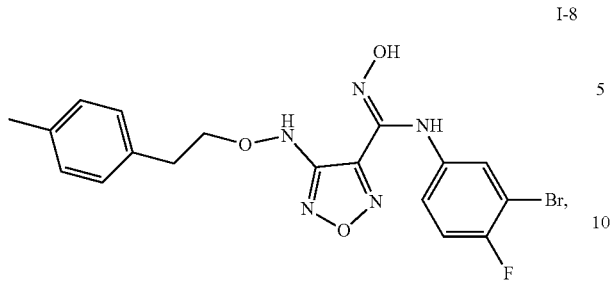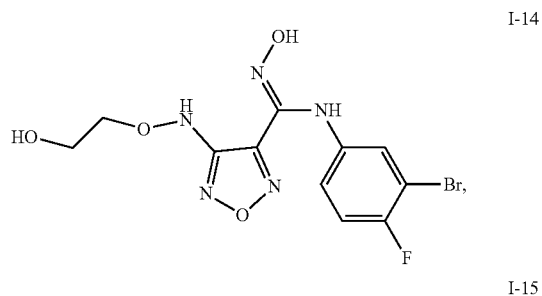

I-20
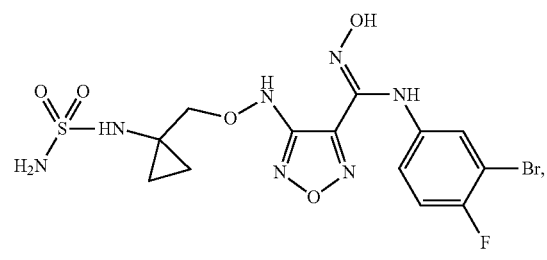
I-21
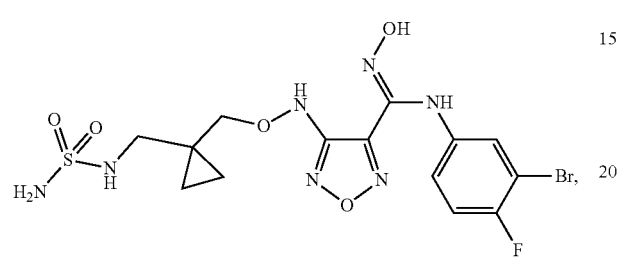
I-22
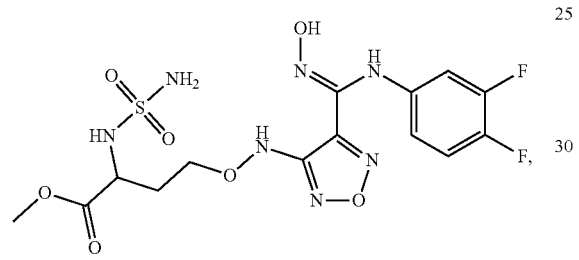
I-23
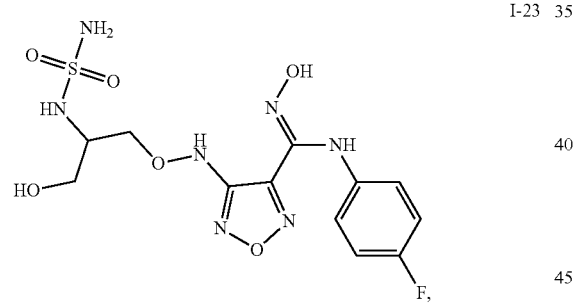
I-24
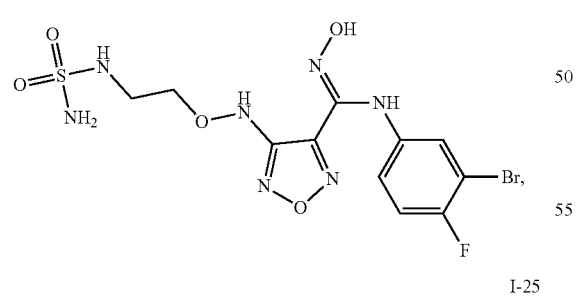
I-25
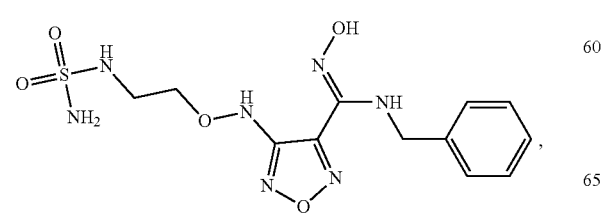
I-26
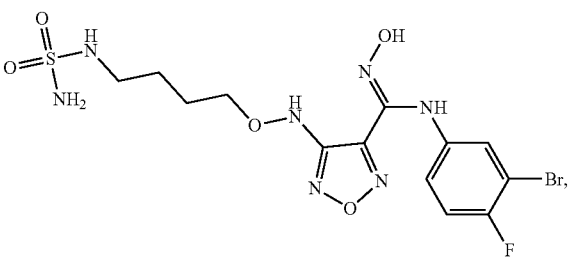
I-27
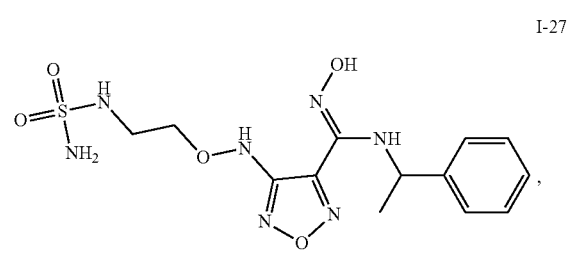
I-28
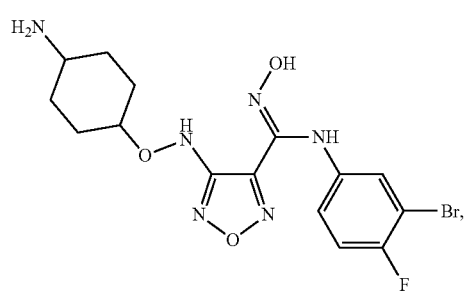
I-29
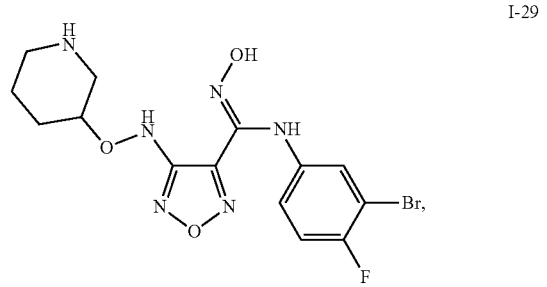
I-30
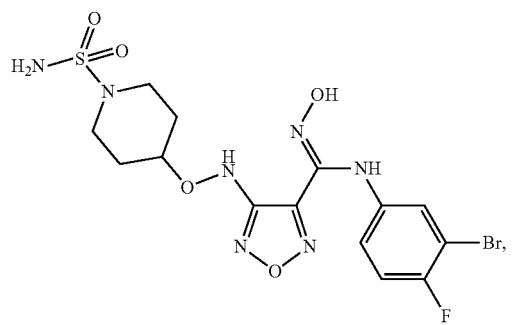

I-31 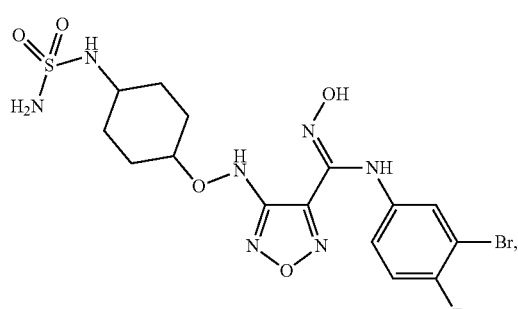
I-32 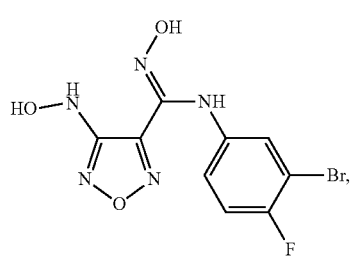
I-33 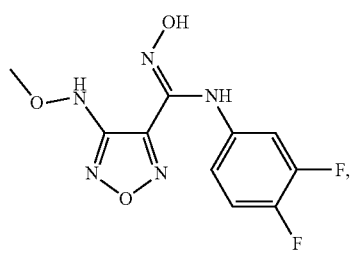
I-34 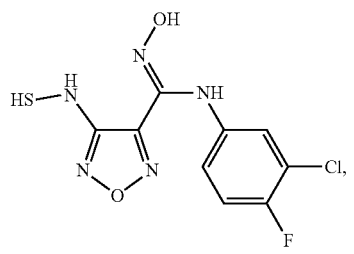
I-35 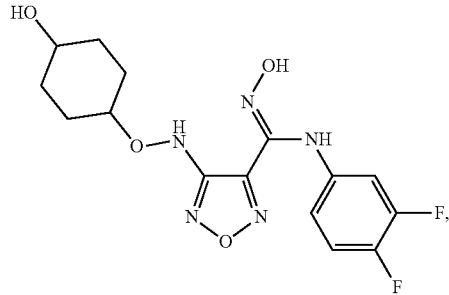
I-36 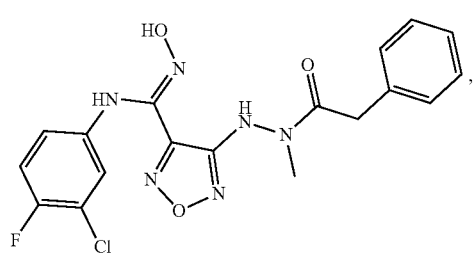
I-37 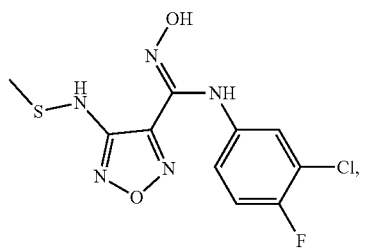
I-38 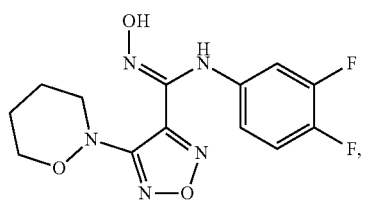
I-39 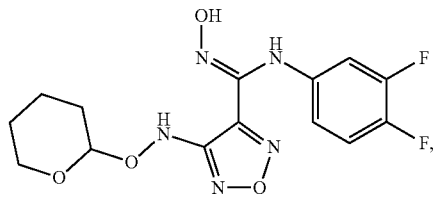
I-40 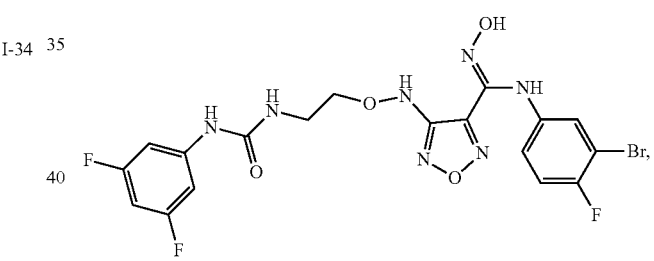
I-41 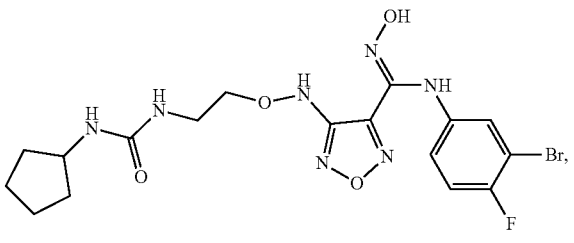
I-42 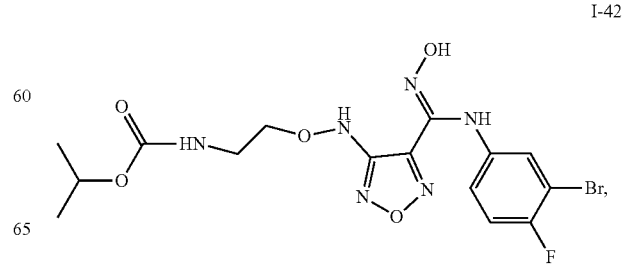

I-43
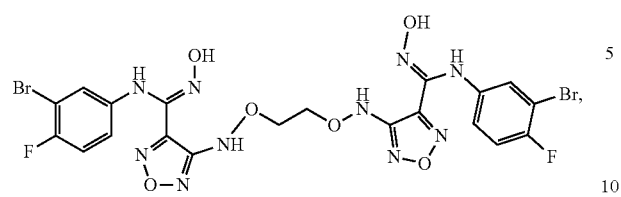

I-44
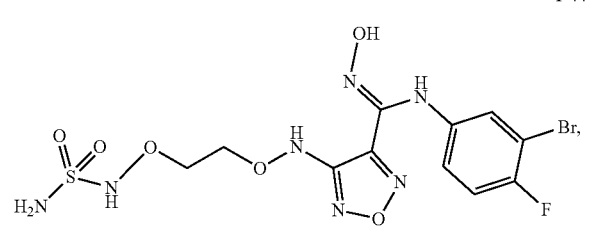

I-45
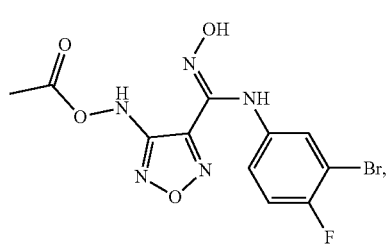

I-46
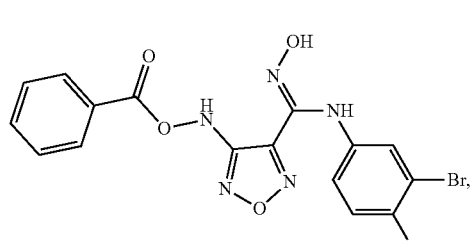

I-47
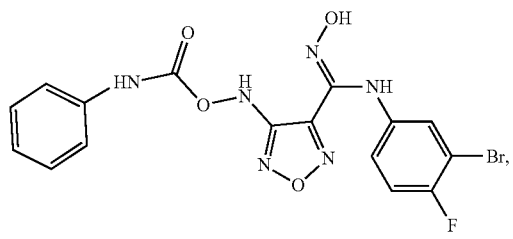

I-48
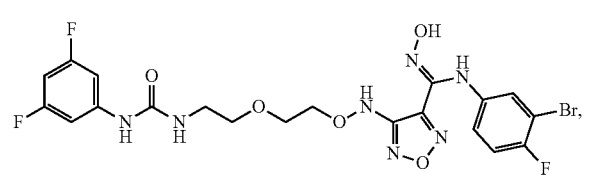

I-49
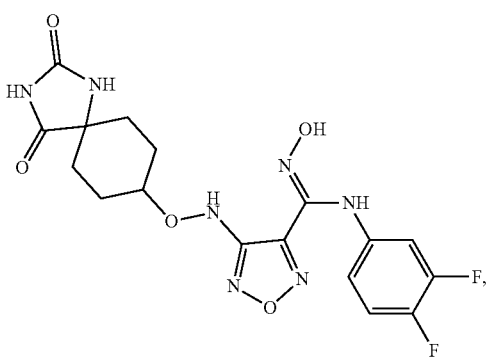

I-50
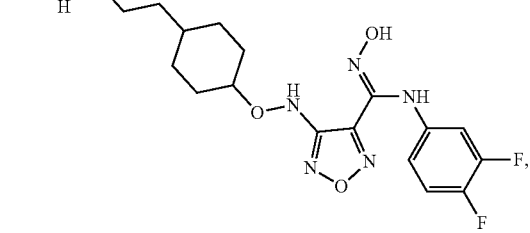

and

I-51
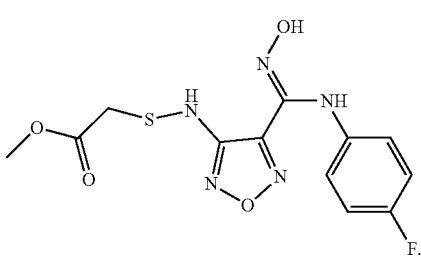

8. A pharmaceutical composition, comprising a therapeutically effective amount of the compound of formula I or formula II, or the pharmaceutically acceptable salt or stereoisomer thereof as an active ingredient, and one or more pharmaceutically acceptable carriers, diluents, or excipients.

9. A method of treating a disease associated with indoleamine 2,3-dioxygenase, comprising administering a therapeutically effective amount of the compound according to claim 1 or a salt or stereoisomer thereof to a subject in need thereof, wherein the disease is a cervical cancer, Alzheimer's disease, depression, or cataract.

10. The method according to claim 9, wherein the compound is selected from
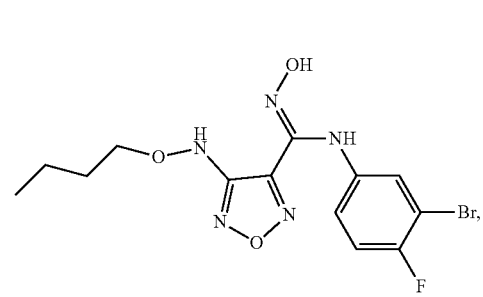
I-1
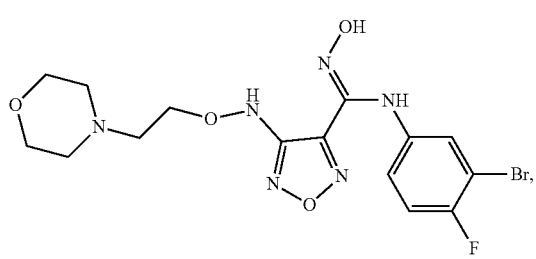
I-2
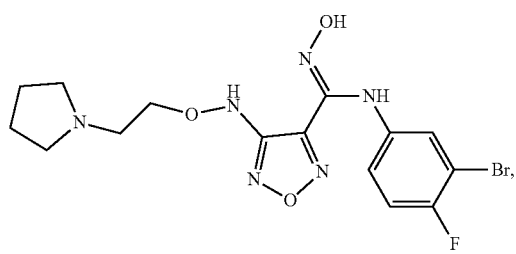
I-3
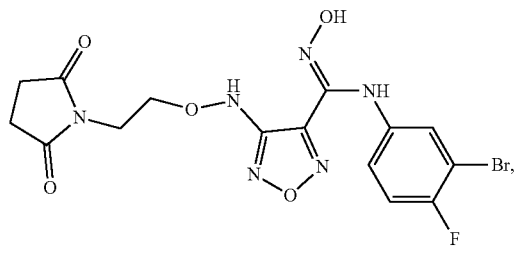
I-4
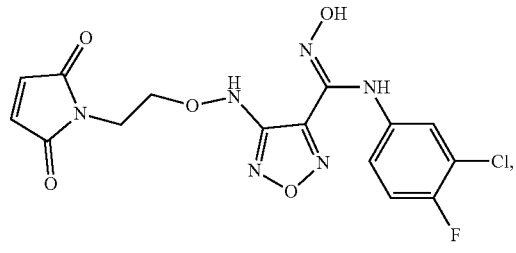
I-5
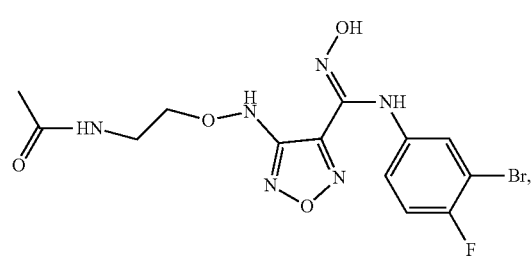
I-6
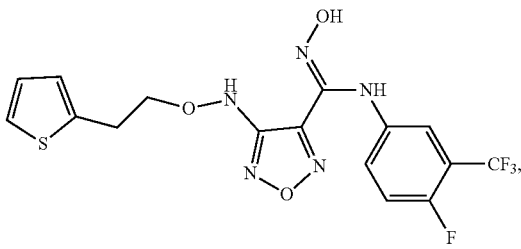
I-7
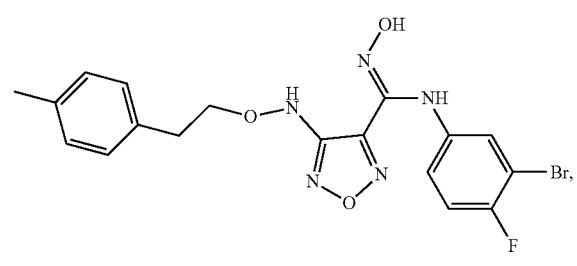
I-8
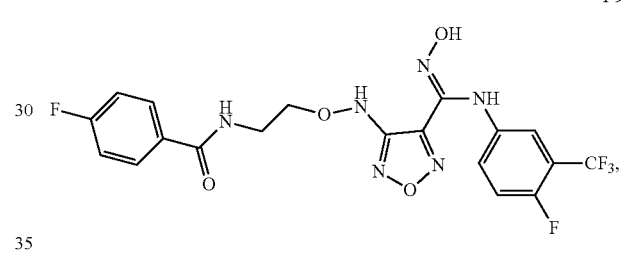
I-9
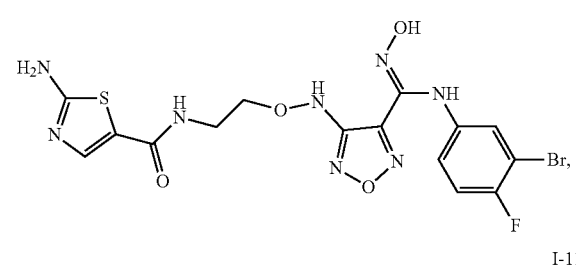
I-10
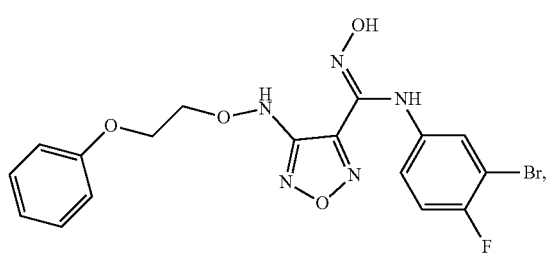
I-11
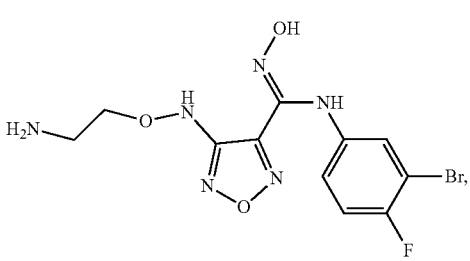
I-12

-continued
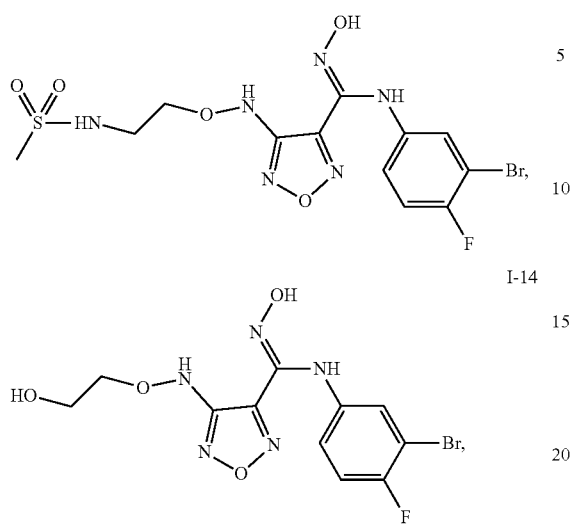
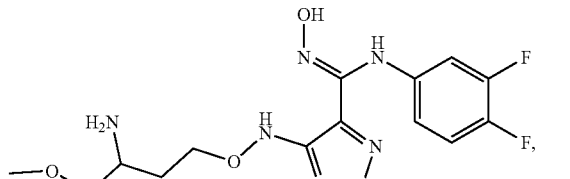
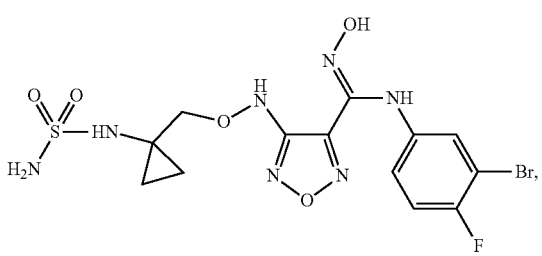
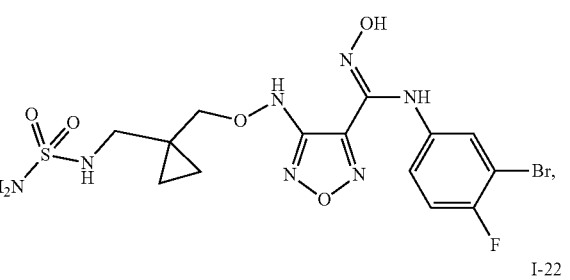
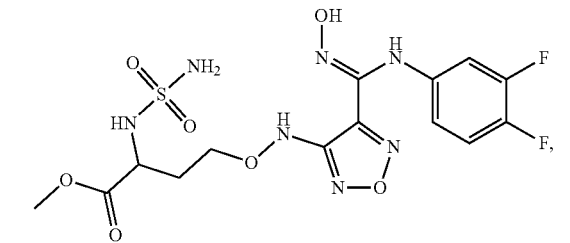
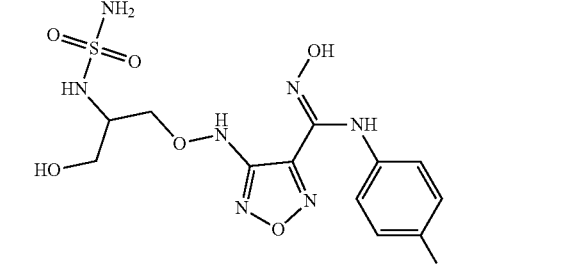
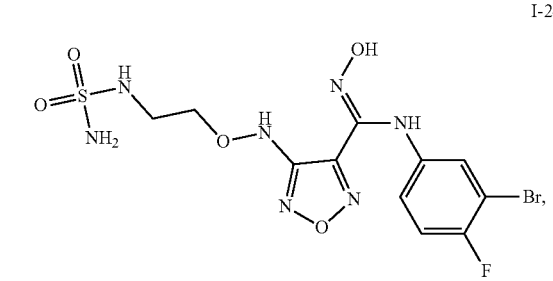

I-25
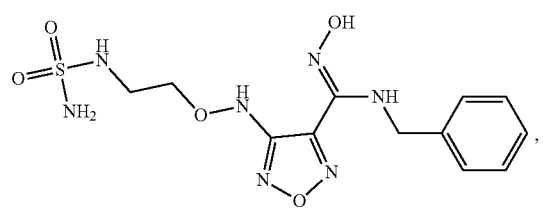
I-26
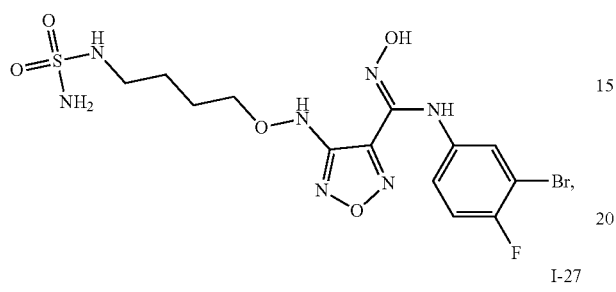
I-27
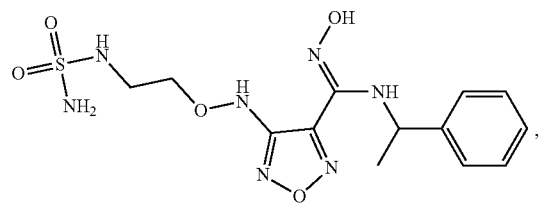
I-28
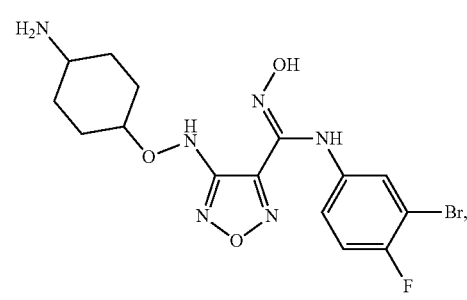
I-29
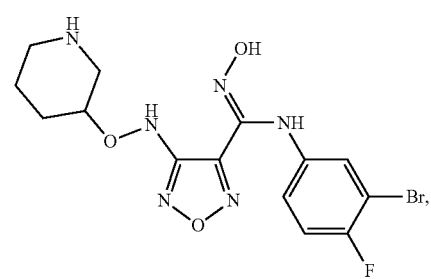
I-30
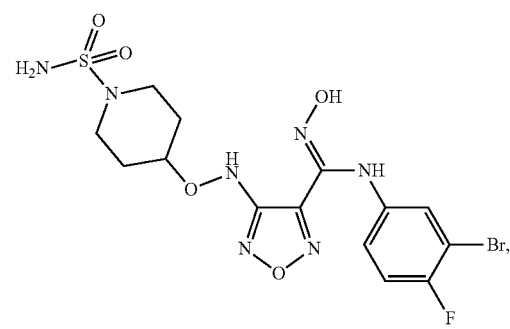
I-31
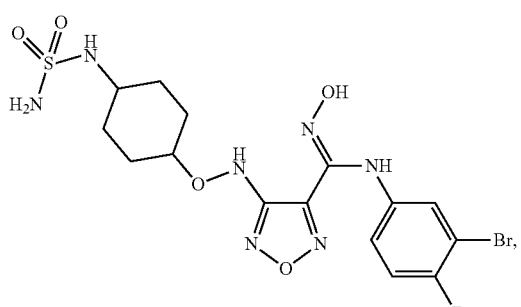
I-32
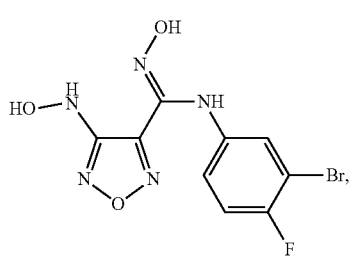
I-33
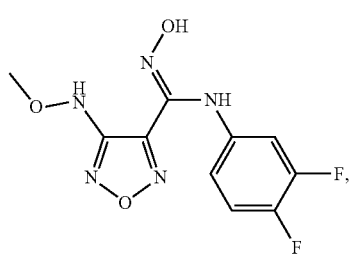
I-34
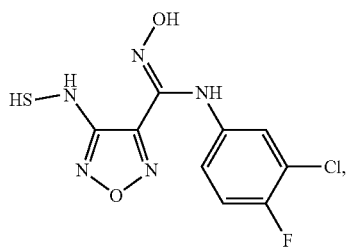
I-35
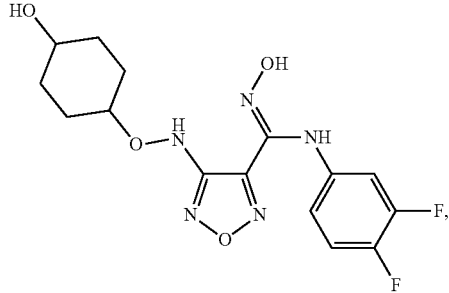
I-36

I-37
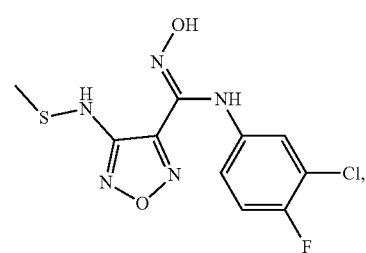
I-38
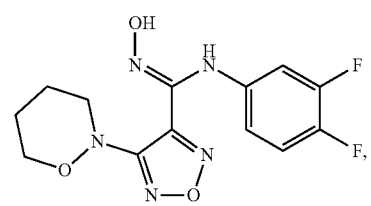
I-39
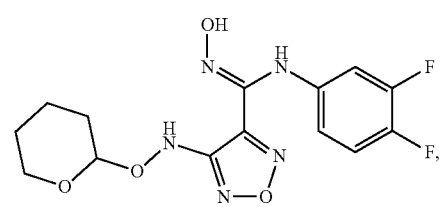
I-40
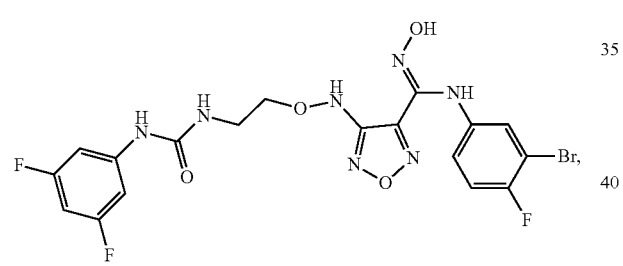
I-41
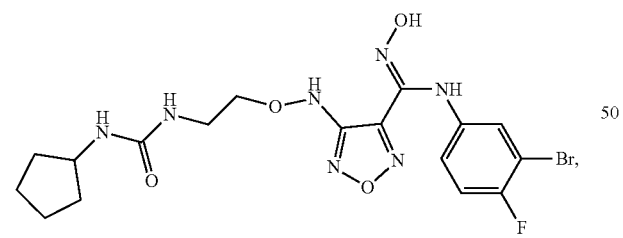
I-42
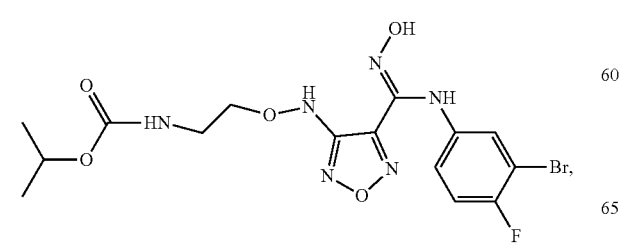
I-43
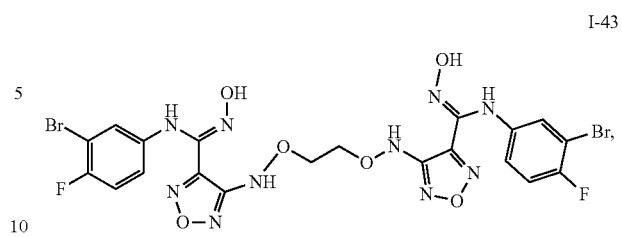
I-44
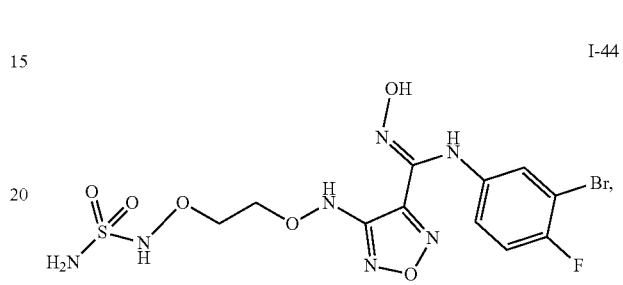
I-45
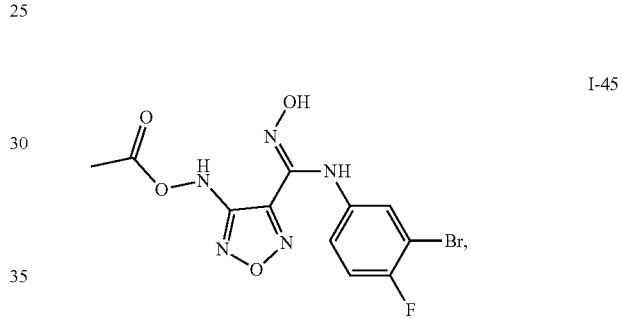
I-46
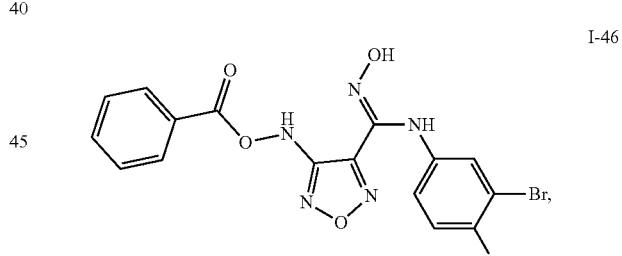
I-47
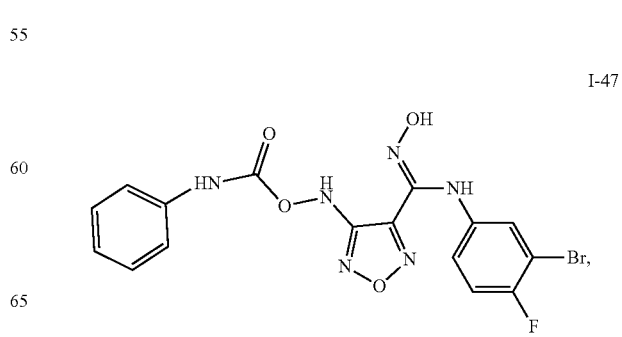

I-48
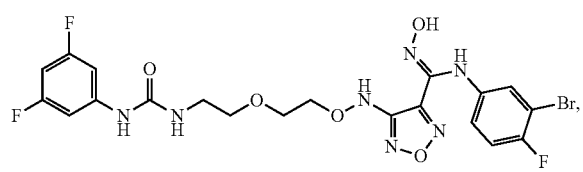
I-50
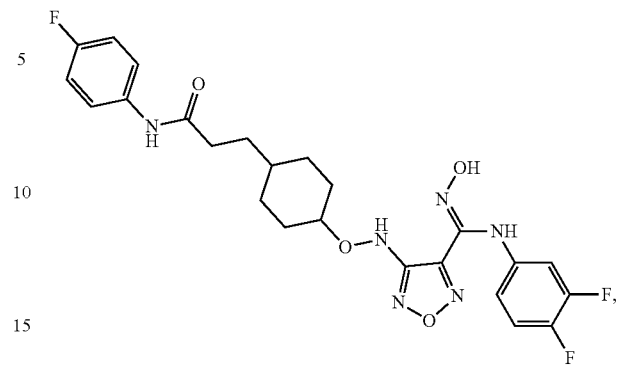
and
I-51
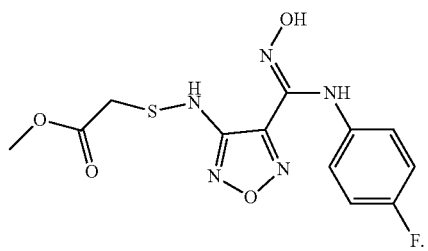
I-49
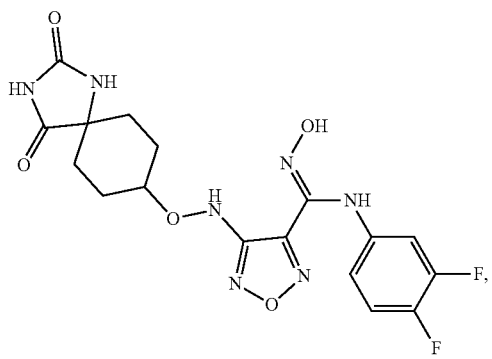
11. A method of treating a disease associated with indoleamine 2,3-dioxygenase, comprising administering a therapeutically effective amount of the compound according to the pharmaceutical composition according to claim 8 to a subject in need thereof, wherein the disease is cervical cancer, Alzheimer's disease, depression, or cataract.
* * * * *